(12) United States Patent
Kim et al.

(10) Patent No.: US 7,894,893 B2
(45) Date of Patent: Feb. 22, 2011

(54) ARRHYTHMIA CLASSIFICATION AND THERAPY SELECTION

(75) Inventors: Jaeho Kim, Redmond, WA (US); Joseph Bocek, Seattle, WA (US); Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 645 days.

(21) Appl. No.: 10/955,831

(22) Filed: Sep. 30, 2004

(65) Prior Publication Data

US 2006/0074331 A1  Apr. 6, 2006

(51) Int. Cl.
   *A61N 1/02* (2006.01)
(52) U.S. Cl. ........................... 607/4; 600/515
(58) Field of Classification Search ............. 600/515; 607/4
   See application file for complete search history.

(56) References Cited

U.S. PATENT DOCUMENTS

| | | | |
|---|---|---|---|
| 4,023,564 A | 5/1977 | Valiquette et al. | |
| 4,336,810 A * | 6/1982 | Anderson et al. | 600/515 |
| 4,428,378 A | 1/1984 | Anderson et al. | |
| 4,550,221 A | 10/1985 | Mabusth | |
| 4,686,332 A | 8/1987 | Greanias et al. | |
| 4,830,006 A | 5/1989 | Haluska et al. | |
| 4,865,036 A | 9/1989 | Chirife | |
| 4,872,459 A | 10/1989 | Pless et al. | |
| 4,880,005 A | 11/1989 | Pless et al. | |
| 5,002,052 A | 3/1991 | Haluska | |
| 5,107,850 A | 4/1992 | Olive | |
| 5,144,947 A | 9/1992 | Wilson | |
| 5,158,092 A | 10/1992 | Glace | |
| 5,161,527 A | 11/1992 | Nappholz et al. | |
| 5,161,529 A | 11/1992 | Stotts et al. | |

(Continued)

FOREIGN PATENT DOCUMENTS

EP  0360412  3/1990

(Continued)

OTHER PUBLICATIONS

M. S. Wathen, M.D. et al. Shock Reduction Using Antitachycardia Pacing for Spontaneous Rapid Ventricular Tachycardia in Patients with Coronary Artery Disease. *Circulation 2001*, vol. 104:796-801. © 2001 American Heart Association, Inc.

(Continued)

*Primary Examiner*—Eric D. Bertram
(74) *Attorney, Agent, or Firm*—Hollingsworth & Funk, LLC

(57) ABSTRACT

Different types of cardiac arrhythmia are classified based on the morphology of the arrhythmic beats. Cardiac beats associated with an arrhythmic episode are compared to a plurality of representative beat morphologies, each representative beat morphology characterizing a type of arrhythmia of the heart. An arrhythmic episode may be classified as a particular type of arrhythmia if the morphology of the arrhythmic cardiac beats matches a representative beat morphology characterizing the particular type of arrhythmia. An appropriate therapy for the particular type of arrhythmia may be selected based on the arrhythmia classification. A particular type of arrhythmia may be associated with one or more therapies used to treat the arrhythmia. The therapy used to treat the arrhythmia may comprise a therapy identified as a previously successful therapy.

17 Claims, 16 Drawing Sheets

U.S. PATENT DOCUMENTS

| | | |
|---|---|---|
| 5,176,137 A | 1/1993 | Erickson et al. |
| 5,181,511 A | 1/1993 | Nickolls et al. |
| 5,193,550 A | 3/1993 | Duffin |
| 5,209,229 A | 5/1993 | Gilli |
| 5,217,021 A * | 6/1993 | Steinhaus et al. ............ 600/515 |
| 5,222,493 A | 6/1993 | Sholder |
| 5,224,475 A | 7/1993 | Berg et al. |
| 5,251,624 A | 10/1993 | Bocek et al. |
| 5,257,621 A | 11/1993 | Bardy et al. |
| 5,312,441 A | 5/1994 | Mader et al. |
| 5,312,445 A | 5/1994 | Nappholz et al. |
| 5,324,310 A | 6/1994 | Greeninger et al. |
| 5,330,505 A | 7/1994 | Cohen |
| 5,330,508 A | 7/1994 | Gunderson |
| 5,342,402 A | 8/1994 | Olson et al. |
| 5,350,410 A | 9/1994 | Kleks et al. |
| 5,379,776 A | 1/1995 | Murphy et al. |
| 5,411,031 A | 5/1995 | Yomtov |
| 5,425,749 A | 6/1995 | Adams |
| 5,447,519 A | 9/1995 | Peterson |
| 5,458,620 A | 10/1995 | Adams et al. |
| 5,472,453 A | 12/1995 | Alt |
| 5,513,644 A | 5/1996 | McClure et al. |
| 5,548,619 A | 8/1996 | Horiike et al. |
| 5,554,177 A | 9/1996 | Kieval |
| 5,587,970 A | 12/1996 | Greenwood |
| 5,662,688 A | 9/1997 | Haefner et al. |
| 5,683,424 A | 11/1997 | Brown et al. |
| 5,683,431 A | 11/1997 | Wang |
| 5,685,315 A | 11/1997 | McClure et al. |
| 5,725,559 A | 3/1998 | Alt et al. |
| 5,755,737 A | 5/1998 | Prieve et al. |
| 5,779,645 A | 7/1998 | Olson et al. |
| 5,782,888 A | 7/1998 | Sun et al. |
| 5,817,027 A | 10/1998 | Arand et al. |
| 5,836,971 A | 11/1998 | Starkweather |
| 5,844,506 A | 12/1998 | Binstead |
| 5,846,263 A | 12/1998 | Peterson et al. |
| 5,855,593 A | 1/1999 | Olson et al. |
| 5,857,977 A | 1/1999 | Caswell et al. |
| 5,871,512 A | 2/1999 | Hemming et al. |
| 5,893,882 A | 4/1999 | Peterson et al. |
| 5,978,707 A | 11/1999 | Krig et al. |
| 5,999,854 A | 12/1999 | Deno et al. |
| 6,064,906 A | 5/2000 | Langberg et al. |
| 6,076,014 A | 6/2000 | Alt |
| 6,101,414 A | 8/2000 | Kroll |
| 6,128,529 A | 10/2000 | Esler |
| 6,137,308 A | 10/2000 | Nayak |
| 6,147,680 A | 11/2000 | Tareev |
| 6,151,524 A | 11/2000 | Krig et al. |
| 6,167,308 A | 12/2000 | Degroot |
| 6,178,350 B1 | 1/2001 | Olson et al. |
| 6,185,459 B1 | 2/2001 | Mehra et al. |
| 6,192,273 B1 | 2/2001 | Igel et al. |
| 6,192,275 B1 | 2/2001 | Zhu et al. |
| 6,212,428 B1 | 4/2001 | Hsu et al. |
| 6,221,011 B1 | 4/2001 | Bardy |
| 6,223,078 B1 | 4/2001 | Marcovecchio |
| 6,230,055 B1 | 5/2001 | Sun et al. |
| 6,253,102 B1 | 6/2001 | Hsu et al. |
| 6,266,554 B1 | 7/2001 | Hsu et al. |
| 6,270,457 B1 | 8/2001 | Bardy |
| 6,275,732 B1 | 8/2001 | Hsu et al. |
| 6,277,072 B1 | 8/2001 | Bardy |
| 6,280,380 B1 | 8/2001 | Bardy |
| 6,289,248 B1 | 9/2001 | Conley et al. |
| 6,308,095 B1 | 10/2001 | Hsu et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,393,316 B1 | 5/2002 | Gillberg et al. |
| 6,398,728 B1 | 6/2002 | Bardy |
| 6,400,986 B1 | 6/2002 | Sun et al. |
| 6,418,340 B1 | 7/2002 | Conley et al. |
| 6,434,417 B1 | 8/2002 | Lovett |
| 6,438,407 B1 | 8/2002 | Ousdigian et al. |
| 6,438,410 B2 | 8/2002 | Hsu et al. |
| 6,440,066 B1 | 8/2002 | Bardy |
| 6,445,949 B1 | 9/2002 | Kroll |
| 6,449,503 B1 | 9/2002 | Hsu |
| 6,477,422 B1 | 11/2002 | Splett |
| 6,480,734 B1 | 11/2002 | Zhang et al. |
| 6,487,443 B2 | 11/2002 | Olson et al. |
| 6,490,478 B1 | 12/2002 | Zhang et al. |
| 6,564,106 B2 | 5/2003 | Guck et al. |
| 6,594,523 B1 | 7/2003 | Levine |
| 6,611,713 B2 | 8/2003 | Schauerte |
| 6,631,290 B1 | 10/2003 | Guck et al. |
| 6,636,764 B1 | 10/2003 | Fain et al. |
| 6,654,639 B1 | 11/2003 | Lu |
| 6,684,100 B1 | 1/2004 | Sweeney et al. |
| 6,708,058 B2 | 3/2004 | Kim et al. |
| 6,731,982 B1 | 5/2004 | Kroll et al. |
| 6,766,194 B1 | 7/2004 | Kroll |
| 6,801,806 B2 | 10/2004 | Sun et al. |
| 6,882,883 B2 | 4/2005 | Condie et al. |
| 6,885,890 B2 | 4/2005 | Spinelli et al. |
| 6,888,538 B2 | 5/2005 | Ely et al. |
| 6,889,079 B2 | 5/2005 | Bocek et al. |
| 6,909,916 B2 | 6/2005 | Spinelli |
| 6,922,585 B2 | 7/2005 | Zhou |
| 6,993,385 B1 | 1/2006 | Routh |
| 7,031,764 B2 | 4/2006 | Schwartz et al. |
| 7,031,771 B2 | 4/2006 | Brown et al. |
| 7,076,289 B2 | 7/2006 | Sakar et al. |
| 7,085,599 B2 | 8/2006 | Kim et al. |
| 6,084,253 A1 | 9/2006 | Johnson et al. |
| 7,103,405 B2 | 9/2006 | Sakar et al. |
| 7,107,098 B2 | 9/2006 | Sharma et al. |
| 7,129,935 B2 | 10/2006 | Mackey |
| 7,130,677 B2 | 10/2006 | Brown et al. |
| 7,130,678 B2 | 10/2006 | Ritscher et al. |
| 7,184,815 B2 | 2/2007 | Kim et al. |
| 7,228,173 B2 | 6/2007 | Cazares |
| 7,277,747 B2 | 10/2007 | Cazares et al. |
| 7,330,757 B2 | 2/2008 | Ostroff et al. |
| 7,477,932 B2 | 1/2009 | Lee et al. |
| 7,558,623 B2 | 7/2009 | Fischell et al. |
| 7,706,866 B2 | 4/2010 | Zhang et al. |
| 7,725,184 B2 | 5/2010 | Cazares |
| 7,729,762 B2 | 6/2010 | Sun |
| 2002/0183637 A1 | 12/2002 | Kim et al. |
| 2003/0120316 A1 | 6/2003 | Spinelli et al. |
| 2003/0191403 A1 | 10/2003 | Zhou et al. |
| 2004/0093035 A1 | 5/2004 | Schwartz et al. |
| 2004/0111119 A1 | 6/2004 | Sakar |
| 2004/0111120 A1 | 6/2004 | Sakar |
| 2004/0111121 A1 | 6/2004 | Brown |
| 2004/0167579 A1 | 8/2004 | Sharma et al. |
| 2004/0176694 A1 | 9/2004 | Kim et al. |
| 2004/0215270 A1 | 10/2004 | Ritscher et al. |
| 2005/0131476 A1 | 6/2005 | Kim et al. |
| 2005/0137485 A1 | 6/2005 | Cao |
| 2005/0137641 A1 | 6/2005 | Naughton |
| 2005/0192506 A1 | 9/2005 | Kim et al. |
| 2006/0069322 A1 | 3/2006 | Zhang et al. |
| 2006/0074331 A1 | 4/2006 | Kim et al. |
| 2006/0111747 A1 | 5/2006 | Cazares et al. |
| 2006/0217621 A1 | 9/2006 | Kim |
| 2006/0253044 A1 | 11/2006 | Zhang et al. |
| 2006/0281998 A1 | 12/2006 | Li et al. |
| 2007/0049974 A1 | 3/2007 | Li et al. |

| | | |
|---|---|---|
| 2007/0142736 | A1 | 6/2007 Cazares |

FOREIGN PATENT DOCUMENTS

| | | |
|---|---|---|
| EP | 0 450 943 A2 | 4/1991 |
| EP | 0 450 943 B2 | 4/1991 |
| EP | 0 547 733 A2 | 6/1993 |
| EP | 0547733 | 6/1993 |
| EP | 0709112 | 5/1996 |
| EP | 0801960 | 10/1997 |
| EP | 1 267 993 B1 | 3/2001 |
| EP | 1112755 | 7/2001 |
| WO | WO9840122 | 9/1998 |
| WO | WO 02/24276 | 3/2002 |
| WO | 03047690 | 6/2003 |
| WO | WO 03/047690 A2 | 6/2003 |
| WO | WO2006039694 | 4/2006 |

OTHER PUBLICATIONS

Martha Kerr. Shock Rate Cut 70% with ICDs Programmed to First Deliver Antitachycardia Pacing: Results of the PainFREE Rx II Trial. NewsRhythms. MedScape CRM News 2003. www.medscape.com.
U.S. Appl. No. 11/151,102.
U.S. Appl. No. 11/038,996.
U.S. Appl. No. 11/312,280, filed Dec. 20, 2005, Cazares et al.
U.S. Appl. No. 11/312,279, filed Dec. 20, 2005, Cazares et al.
U.S. Appl. No. 10/995,655, filed Nov. 23, 2004, Cazares.
U.S. Appl. No. 11/209,976, filed Aug. 23, 2005, Li et al.
U.S. Appl. No. 10/995,704, filed Nov. 23, 2005, Cazares et al.
U.S. Appl. No. 11/089,185, filed Mar. 24, 2005, Kim et al.
"Vitality 2 Implantable Cardioverter Defibrillator System Guide", Guidant Corporation, 2004, Cover pages and pp. 3-15 to 3-19.
Gold, Michael R., et al., "Advanced Rhythm Discrimination for Implantable Cardioverter Defibrillators Using Electrogram Vector Timing and Correlation", *Journal of Cardiovascular Electrophysiology*, vol. 13, No. 11, Nov. 2002, pp. 1092-1097.
Lake et al., *Am. J. Physiol. Regul. Integr. Comp. Physiol.*, 283: R789-97 (2002).
Richman et al., *Am. J. Physiol. Heart Circ. Physiol.*, 278: H2039-49 (2000).
Office Action dated Mar. 28, 2008 from U.S. Appl. No. 11/089,185, 8 pages.
Office Action Response dated Jun. 30, 2008 from U.S. Appl. No. 11/089,185, 13 pages.
Office Action dated Dec. 8, 2008 from U.S. Appl. No. 11/089,185, 6 pages.
Office Action Response dated Apr. 8, 2009 from U.S. Appl. No. 11/089,185, 9 pages.
Office Action dated May 15, 2009 from U.S. Appl. No. 11/089,185, 6 pages.
Office Action dated Jul. 24, 2009 from U.S. Appl. No. 11/089,185, 2 pages.
Office Action Response dated Aug. 4, 2009 from U.S. Appl. No. 11/089,185, 10 pages.
Office Action dated Nov. 3, 2009 U.S. Appl. No. 11/089,185, 6 pages.
Office Action dated Jan. 13, 2010 from U.S. Appl. No. 11/089,185, 3 pages.
Office Action Response dated Jan. 27, 2010 from U.S. Appl. No. 11/089,185, 10 pages.
Office Action dated Mar. 24, 2010 from U.S. Appl. No. 11/089,185, 6 pages.
Office Action Response dated May 20, 2010 from U.S. Appl. No. 11/089,185, 11 pages.
Notice of Allowance dated Jun. 11, 2010 from U.S. Appl. No. 11/089,185, 4 pages.
Notice of Allowance dated Jul. 22, 2010 from U.S. Appl. No. 11/089,185, 4 pages.
Office Action dated Jul. 18, 2006 from U.S. Appl. No. 10/995,655, 9 pages.
Office Action Response dated Oct. 23, 2006 from U.S. Appl. No. 10/995,655, 14 pages.
Notice of Allowance dated Jan. 9, 2007 from U.S. Appl. No. 10/995,655, 9 pages.
Office Action dated Sep. 11, 2009 from U.S. Appl. No. 11/807,696, 10 pages.
Office Action dated Nov. 23, 2009 from U.S. Appl. No. 11/807,696, 3 pages.
Office Action Response dated Dec. 11, 2009 from U.S. Appl. No. 11/807,696, 9 pages.
Notice of Allowance dated Jan. 15, 2010 from U.S. Appl. No. 11/807,696, 7 pages.
Office Action dated Feb. 13, 2007 from U.S. Appl. No. 10/995,704, 9 pages.
Office Action Response dated May 18, 2007 from U.S. Appl. No. 10/995,704, 17 pages.
Office Action dated Aug. 23, 2007 from U.S. Appl. No. 10/995,704, 8 pages.
Office Action Response dated Oct. 25, 2007 from U.S. Appl. No. 10/995,704, 12 pages.
Office Action dated Nov. 20, 2007 from U.S. Appl. No. 10/995,704, 3 pages.
Pre-Appeal Brief dated Jan. 28, 2008 from U.S. Appl. No. 10/995,704, 6 pages.
Appeal Brief date Apr. 25, 2008 from U.S. Appl. No. 10/995,704, 30 pages.
Examiner Answer dated Jul. 25, 2008 from U.S. Appl. No. 10/995,704, 8 pages.
Reply Brief dated Sep. 25, 2008 from U.S. Appl. No. 10/995,704, 10 pages.
Office Action dated Jan. 29, 2009 from U.S. Appl. No. 11/312,279, 9 pages.
Office Action dated Apr. 9, 2009 from U.S. Appl. No. 11/312,279, 2 pages.
Office Action Response dated Apr. 28, 2009 from U.S. Appl. No. 11/312,279, 10 pages.
Office Action dated Aug. 19, 2009 from U.S. Appl. No. 11/312,279, 13 pages.
Office Action Response dated Jan. 14, 2010 from U.S. Appl. No. 11/312,279, 14 pages.
Office Action dated Apr. 22, 2008 from U.S. Appl. No. 11/209,976, 9 pages.
Office Action Response dated May 27, 2008 from U.S. Appl. No. 11/209,976, 7 pages.
Office Action dated Aug. 29, 2008 from U.S. Appl. No. 11/209,976, 10 pages.
Office Action Response dated Dec. 18, 2008 from U.S. Appl. No. 11/209,976, 11 pages.
Office Action dated Apr. 16, 2009 from U.S. Appl. No. 11/209,976, 9 pages.
Office Action dated Jul. 10, 2009 from U.S. Appl. No. 11/209,976, 10 pages.
Office Action Response dated Sep. 3, 2009 from U.S. Appl. No. 11/209,976, 7 pages.
Office Action dated Nov. 20, 2009 from U.S. Appl. No. 11/209,976, 10 pages.
Office Action Response dated Feb. 17, 2010 from U.S. Appl. No. 11/209,976, 10 pages.
Office Action dated Apr. 22, 2010 from U.S. Appl. No. 11/209,976, 12 pages.
Office Action Response dated Jun. 22, 2010 from U.S. Appl. No. 11/209,976, 11 pages.
Office Action dated Jul. 13, 2010 from U.S. Appl. No. 11/209,976, 4 pages.
Office Action dated May 1, 2008 from U.S. Appl. No. 11/267,071, 7 pages.
Office Action dated Sep. 24, 2008 from U.S. Appl. No. 11/267,071, 2 pages.
Office Action Response dated Oct. 23, 2008 from U.S. Appl. No. 11/267,071, 13 pages.
Office Action dated Jan. 16, 2009 from U.S. Appl. No. 11/267,071, 8 pages.
Office Action Response dated Apr. 15, 2009 from U.S. Appl. No. 11/267,071, 9 pages.
Office Action dated Jun. 12, 2009 from U.S. Appl. No. 11/267,071, 5 pages.

Office Action Response dated Sep. 10, 2009 from U.S. Appl. No. 11/267,071, 10 pages.
Notice of Allowance dated Dec. 17, 2009 from U.S. Appl. No. 11/267,071, 4 pages.
Office Action dated Jun. 16, 2009 from European Application No. 05800765.9, 3 pages.
Office Action Response dated Dec. 15, 2009 from European Application No. 05800765.9, 39 pages.
Office Action Response dated Sep. 1, 2008 from European Application No. 06839301.6, 12 pages.
International Preliminary Report on Patentability dated Apr. 12, 2007 from PCT Application No. PCT/US2005/035641, 9 pages.
International Preliminary Report on Patentability dated Jul. 3, 2008 from PCT Application No. PCT/US2006/047215, 8 pages.
International Preliminary Report on Patentability dated Mar. 6, 2008 from PCT Application No. PCT/US2006/032872, 6 pages.
International Search Report and Written Opinion dated Jun. 12, 2006 from PCT Application No. PCT/US2005/035641, 20 pages.
International Search Report and Written Opinion dated Jun. 19, 2007 from PCT Application No. PCT/US2006/047215, 13 pages.
International Search Report and Written Opinion dated Feb. 12, 2007 from PCT Application No. PCT/US2006/032872, 8 pages.
Invitation to Pay Additional Fees dated Jan. 3, 2006 from PCT Application No. PCT/US2005/035641, 8 pages.
Dubin, Rapid Interpretation of EKG's, 2000, Cover Publishing Company, 6th edition, p. 3334-3345.
Lake et al., Sample entropy analysis of neonatal heart rate variability, An. J. Physiol Reguul Integr omp Physiol., vol. 283, 2002.
Mercando et al., Measurement of Differences in Timing and Sequence Between Two Ventricular Electrodes as a Means of Tachycardia Differentiation, PACE, Part II, vol. 9, Nov.-Dec. 1986, 1069-1078. (abstract only).
Appeal Decision dated Sep. 8, 2010 from U.S. Appl. No. 10/995,704, 6 pages.
Office Action Response submitted Sep. 15, 2010 from U.S. Appl. No. 11/209,976, 9 pages.
Notice of Allowance dated Dec. 22, 2010 from U.S. Appl. No. 10/995,704, 6 pages.

* cited by examiner

ARRHYTHMIA CLASSIFICATION AND THERAPY SELECTION

FIELD OF THE INVENTION

The present invention relates generally to implantable medical devices, and more particularly, to classifying cardiac rhythms and providing arrhythmia therapy.

BACKGROUND OF THE INVENTION

Rhythmic contractions of a healthy heart are normally initiated by the sinoatrial (SA) node, specialized cells located in the upper right atrium. The SA node is the normal pacemaker of the heart. When functioning normally, the heart produces rhythmic contractions and is capable of pumping blood throughout the body. However, due to disease or injury, the heart rhythm may become irregular resulting in diminished blood circulation. Arrhythmia is a general term used to describe heart rhythm irregularities arising from a variety of physical conditions and disease processes.

A cardiac tachyarrhythmia that originates in a non-ventricular region of the heart is denoted a supra-ventricular tachyarrhythmia (SVT). Atrial fibrillation and atrial flutter are examples of SVT. Both conditions are characterized by rapid contractions of the atria resulting in hemodynamically inefficient pumping action.

Cardiac arrhythmias originating in a ventricular region of the heart are denoted ventricular tachyarrhythmias (VT). Some types of ventricular tachyarrhythmia are characterized by rapid ventricular contractions that are fairly regular and coordinated. Such rhythms can degenerate into ventricular fibrillation (VF). Ventricular fibrillation produces extremely rapid, non-coordinated contractions of the ventricles and is fatal unless the heart is returned to sinus rhythm within a few minutes.

Implantable cardiac rhythm management (CRM) devices, including pacemakers and implantable cardioverter/defibrillators (ICDs), have been used to deliver effective treatment to patients with serious cardiac arrhythmias. Leads extending into the patient's heart are connected to electrodes electrically coupled to the myocardium for sensing the heart's electrical signals and for delivering stimulation pulses to the heart in accordance with various therapies for treating the arrhythmias.

A number of CRM devices having various modes for sensing and pacing one or more heart chambers can treat cardiac arrhythmias using a variety of tiered therapies. These tiered therapies range from the delivery of low energy pacing pulses timed to assist the heart in maintaining pumping efficiency to high energy shocks to terminate fibrillation. To effectively deliver these treatments the CRM device must first identify the type of arrhythmia that is occurring.

For the reasons stated above, and for other reasons stated below which will become apparent to those skilled in the art upon reading the present specification, there is a need in the art for methods and systems that accurately identify and treat cardiac arrhythmias. There exists a further need to deliver proper cardiac therapy. The present invention fulfills these and other needs.

SUMMARY OF THE INVENTION

Various embodiments of present invention are directed to methods and systems for delivering classifying types of cardiac arrhythmia. One embodiment involves a method for discriminating between types of arrhythmia affecting one or more heart chambers. Cardiac beats associated with an arrhythmic episode are detected. The morphology of each cardiac beat is compared to a plurality of representative beat morphologies respectively associated with a plurality of types of arrhythmia. The arrhythmic episode is classified as a particular type of arrhythmia if the morphologies of the cardiac beats are consistent with a representative beat morphology of the particular type of arrhythmia.

Another embodiment of the invention involves a method for delivering cardiac therapy to a patient. The method includes associating one or more cardiac therapies respectively with one or more types of cardiac arrhythmia. Cardiac beats of an arrhythmic episode are detected. The morphology of each detected cardiac beat is compared to a plurality of representative beat morphologies respectively associated with a plurality of types of cardiac arrhythmia. The arrhythmic episode is classified as a particular type of cardiac arrhythmia if the morphologies of the cardiac beats are consistent with a representative beat morphology of the particular type of cardiac arrhythmia. The method includes delivering one or more particular therapies associated with the particular type of cardiac arrhythmia if the arrhythmic episode is classified as the particular type of cardiac arrhythmia.

In another embodiment of the invention a cardiac arrhythmia classification system is implemented to classify arrhythmic episodes. The cardiac arrhythmia classification system includes a sensor system comprising electrodes for electrically coupling to a heart. The sensor system is configured to detect cardiac beats associated with an arrhythmic episode of the heart. An arrhythmia classification processor is coupled to the sensor system. The arrhythmia classification processor is configured to compare the morphology of each cardiac beat to a plurality of representative beat morphologies respectively associated with plurality of types of arrhythmia. The arrhythmia classification processor classifies the arrhythmic episode as a particular type of arrhythmia if the morphologies of the cardiac beats are consistent with a representative beat morphology of a particular type of arrhythmia.

Yet a further embodiment involves a cardiac therapy system. The cardiac therapy system includes a sensor system comprising electrodes for electrically coupling to a heart. The sensor system is configured to detect cardiac beats of an arrhythmic episode of the heart. An arrhythmia classification processor is coupled to the sensor system. The arrhythmia classification processor is configured to compare a morphology of each cardiac beat to plurality of representative beat morphologies respectively associated with a plurality of types of arrhythmia. The classification processor classifies the arrhythmic episode as a particular type of arrhythmia if the morphologies of the cardiac beats are consistent with a representative beat morphology of a particular type of arrhythmia.

A therapy unit is coupled to the arrhythmia classification processor. The therapy unit is configured to associate one or more cardiac therapies respectively with the one or more types of arrhythmia and deliver one or more particular therapies associated with the particular type of arrhythmia if the cardiac beats are characterized as the particular type of arrhythmia.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
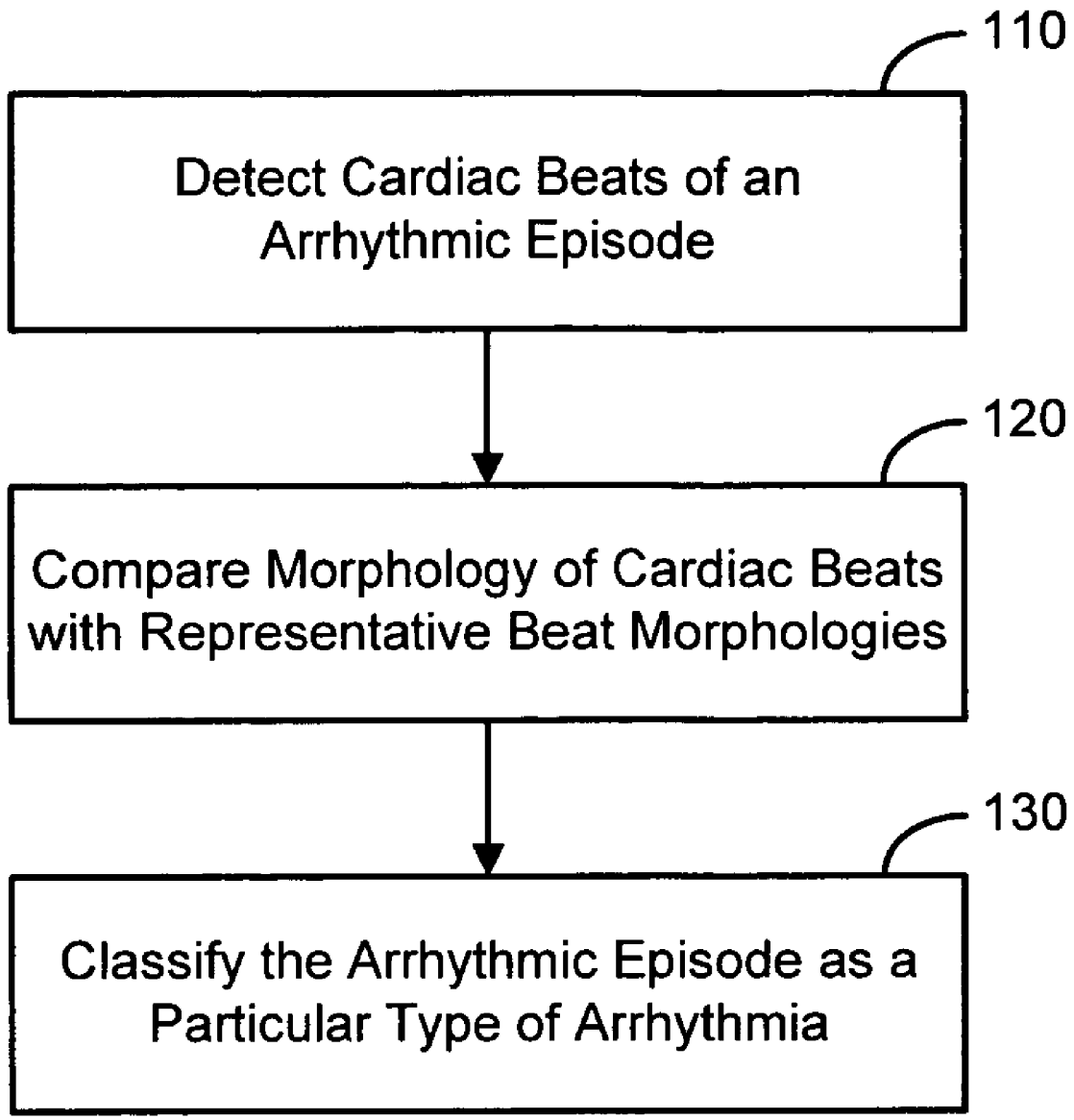
FIGS. 1A-1D are flowcharts of methods for classifying cardiac rhythms and delivering therapy to a patient in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Ventricular tachyarrhythmias are fast heart rhythms that arise within one or more ventricles. Atrial tachyarrhythmias, e.g., atrial flutter or atrial fibrillation, are fast heart rhythms that arise within one or more atria. Cardiac signals representative of ventricular or atrial tachyarrhythmic beats may involve a number of different morphologies. Some types of tachyarrhythmia may be monomorphic. Cardiac signals representing a monomorphic tachyarrhythmia may exhibit a fairly regular rhythm and a similar shape or morphology.

Other types of tachyarrhythmia may comprise multi-morphology or polymorphic ventricular tachyarrhythmia. Each beat of a multi-morphology or polymorphic tachyarrhythmia may be different, making the polymorphic tachyarrhythmia difficult to characterize based on morphology. Ventricular fibrillation is an example of a polymorphic ventricular tachyarrhythmia that presents a disorganized, inconsistent morphology.

Episodes of monomorphic tachyarrhythmia may last only a few beats and may produce minimal symptoms. If the cardiac rate is relatively low, the tachyarrhythmia may be tolerated even if sustained for a number of minutes. Tachyarrhythmia may be treated using a variety of therapies. For example, in some cases, ventricular tachycardia (VT) may be effectively treated by pacing at relatively high energy output when compared to bradycardia pacing. Pacing to mitigate VT may involve one or more pacing bursts and is typically denoted anti-tachycardia pacing (ATP). Other types of VT may require a more aggressive therapy, including high energy cardioversion and/or defibrillation shocks. Still other types of VT may terminate spontaneously without therapy.

The most dangerous form of polymorphic ventricular tachyarrhythmia is ventricular fibrillation, which involves very rapid, small-scale, and uncoordinated contractions. The rapid contractions cause a precipitous drop in blood pressure and low cardiac output. Ventricular fibrillation involving heart rates in excess of about 220 beats per minute rarely terminate spontaneously and may be fatal without rapid therapeutic intervention. Typically therapy for ventricular fibrillation involves a series of high energy defibrillation shocks.

Various embodiments of the invention are directed to an automated process for classifying different types of arrhythmia, e.g., atrial or ventricular tachyarrhythmia. For example, each type of arrhythmia may be associated with a representative beat morphology. A detected arrhythmic episode may be classified as a particular type of arrhythmia by comparing a sample of tachyarrhythmic cardiac beats of the arrhythmic episode with a number of representative beat morphologies associated with the various types of arrhythmia. The arrhythmia may be classified as a particular type of arrhythmia if the sample of the arrhythmic cardiac beats are consistent with the representative beat morphology associated with the particular arrhythmia type.

The flowchart of FIG. 1A illustrates a method of classifying arrhythmia in accordance with embodiments of the invention. As discussed above, various types of arrhythmia, for example, types of monomorphic atrial tachyarrhythmia or monomorphic ventricular tachyarrhythmia, exhibit characteristic beat morphologies that are relatively consistent from beat to beat for a given patient. The representative beat morphologies of various types of monomorphic tachyarrhythmia experienced by the patient may be identified and used to classify subsequent arrhythmic episodes.

An arrhythmic episode may initially be detected using rate criteria. For example, if a heart rate beyond a predetermined threshold is sensed, the episode may be determined to be a tachyarrhythmic episode. The tachyarrhythmic episode may be further classified using morphology criteria. For example, the tachyarrhythmic episode may exhibit a morphology indicative of a particular type of monomorphic tachyarrhythmia. Cardiac beats of the arrhythmic episode may be detected 110 and compared 120 to representative beat morphologies associated with the various types of arrhythmia of the heart. Atrial beats are used to identify types of atrial arrhythmia, ventricular beats are used to identify types of ventricular arrhythmia. If the morphology of the detected cardiac beats is consistent with a particular type of arrhythmia, then the arrhythmic episode is classified 130 as the particular type of arrhythmia.

Figure 1B:
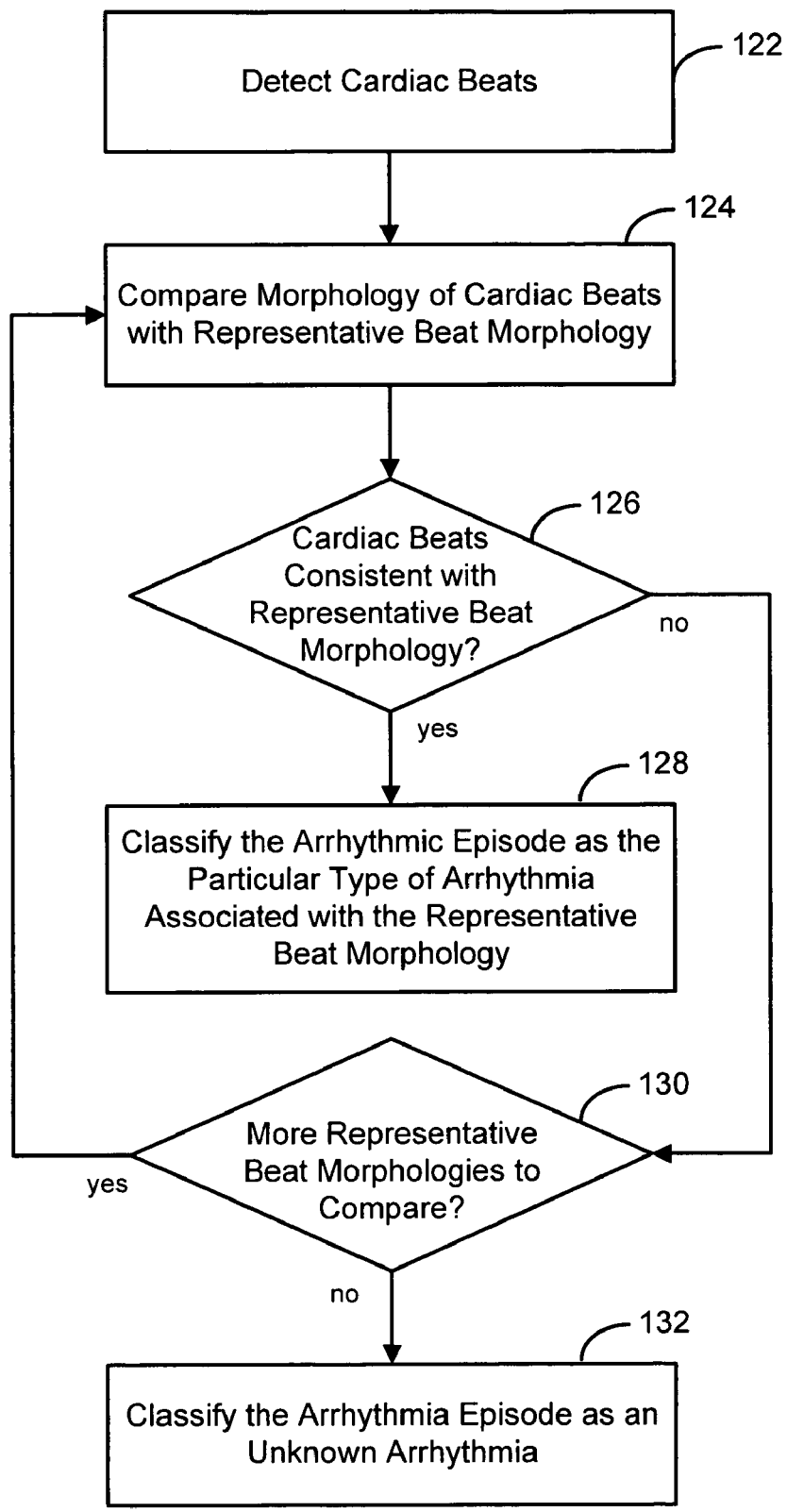

FIG. 1B is a flowchart illustrating another method of classifying arrhythmia in accordance with embodiments of the invention. A sample of cardiac beats of an arrhythmic episode are detected 122. The sample of cardiac beats may comprise sequential or non-sequential beats. The morphology of the detected cardiac beats is compared 124 to a first representative beat morphology associated with a type of arrhythmia. If the morphology of the cardiac beats is consistent 126 with the representative beat morphology, then the arrhythmic episode is classified 128 as the particular type of arrhythmia.

If the cardiac beat morphology is not consistent 126 with the representative beat morphology, and there is another representative beat morphology to compare 130, then the next representative beat morphology is compared 124 to the detected cardiac beats.

If the morphology of the detected cardiac beats does not match any of the representative beat morphologies 130, then the arrhythmic episode comprises an arrhythmia of unknown type. The arrhythmic episode is classified 132 as an unknown or unclassified type of arrhythmia. In one example, the unclassified arrhythmic episode may involve a monomorphic arrhythmia that is characterizable by acquiring a representative beat morphology for the monomorphic arrhythmia. In another example, the unclassified arrhythmic episode may involve a polymorphic arrhythmia, such as ventricular fibrillation, for which characterization using a representative beat morphology may not be achievable.

Various embodiments of the invention are directed to delivering an appropriate therapy for a particular of type of arrhythmia experienced by the patient. In accordance with embodiments of the invention, types of arrhythmia are respectively associated with various therapies used to treat the types of arrhythmia. In a preferred embodiment, a therapy is associated with a particular type of arrhythmia if the therapy is determined to be successful at treating the particular type of arrhythmia.

In one implementation, if a particular type of arrhythmia occurs, then a first therapy assigned to treat the particular type of arrhythmia is delivered to the patient. Additional therapies may be applied in the event that the first therapy does not successfully mitigate the arrhythmia. If a therapy other than the first therapy is successful at terminating or mitigating the arrhythmia, the successful therapy may be used as the first therapy to treat subsequent episodes of the particular type of arrhythmia.

Figure 1C:
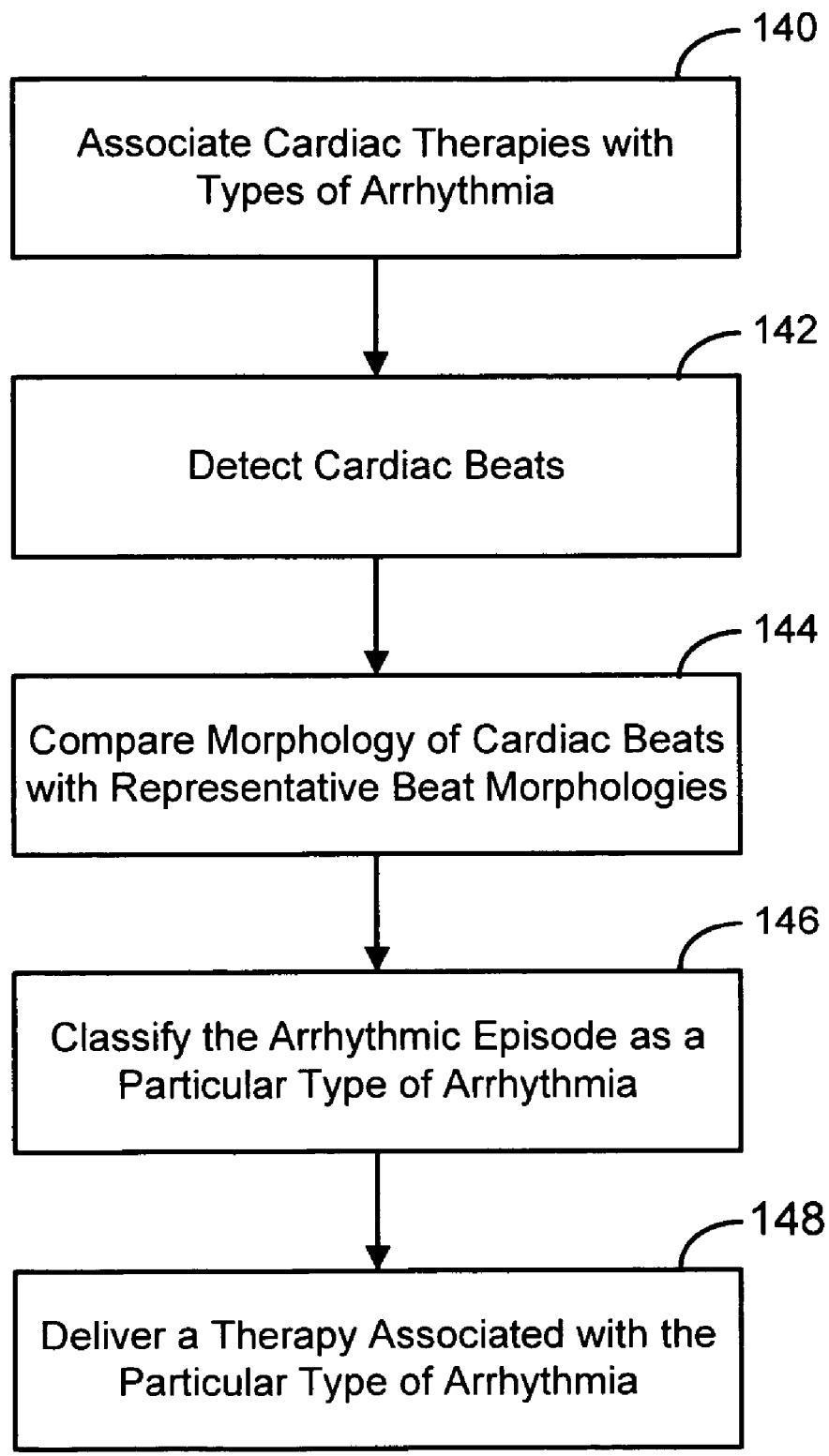

FIG. 1C illustrates a method of delivering cardiac therapy to a patient in accordance with embodiments of the invention. Various cardiac therapies are respectively associated 140 with types of arrhythmia. A representative set of cardiac therapies may involve, for example, antitachycardia pacing (ATP) including burst pacing, (e.g., pacing at 25 Hz or 50 Hz sequences), ramp pacing (e.g., burst pacing with each pace-to-pace interval shortened), scan pacing (e.g., burst pacing with the burst cycle length of each burst shortened between successive bursts, cardioversion shocks (e.g., cardioversion shocks delivered at about 0.5 Joules to about 2 Joules), and titration of defibrillation shocks.

The cardiac beats of an arrhythmic episode are detected 142. The morphology of the detected cardiac beats is compared 144 to representative beat morphologies associated with various types of arrhythmia. The arrhythmic episode is classified 146 as a particular type of arrhythmia based on the comparison. A therapy associated with the particular type of arrhythmia is delivered 148 to the patient.

Figure 1D:
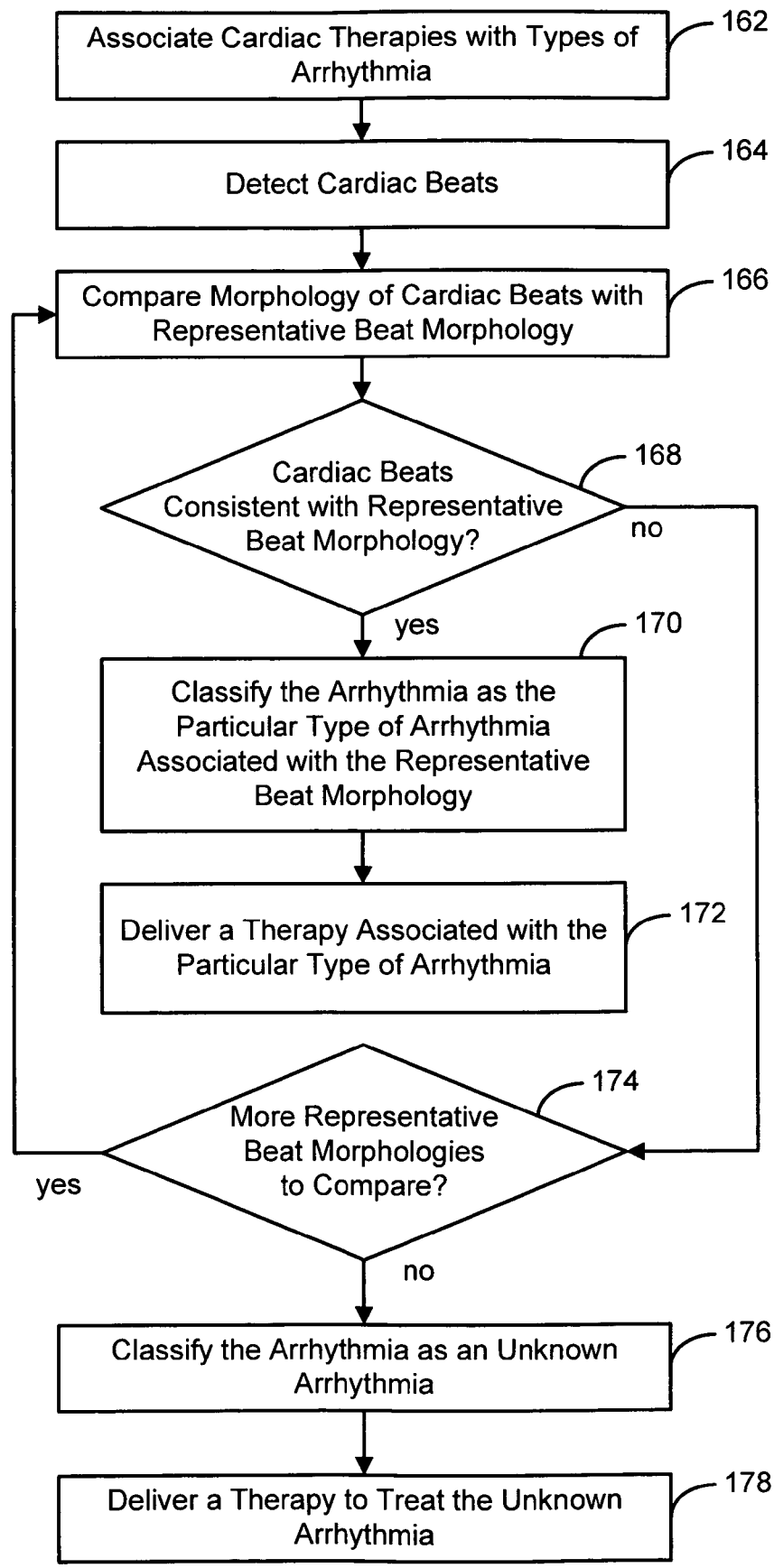

FIG. 1D illustrates another method of delivering cardiac therapy to a patient in accordance with embodiments of the invention. Various cardiac therapies are respectively associated 162 with types of arrhythmia. The cardiac beats of an arrhythmic episode are detected 164. The morphology of the detected cardiac beats is compared 166 to a representative beat morphology associated with a type of VT. If the morphologies of the cardiac beats are consistent 168 with the representative beat morphology, then the arrhythmic episode is classified 170 as the particular type. A therapy associated with the particular type of arrhythmia is delivered 172 to the patient.

If the morphologies of the detected cardiac beats do not match any of the representative beat morphologies 174, then the arrhythmic episode may be classified 176 as an arrhythmia of unknown type and is an unclassified tachyarrhythmia. In one example, the unclassified arrhythmic episode may involve a monomorphic arrhythmia that is characterizable if a representative beat morphology for the monomorphic arrhythmia were acquired. In another example, the unclassified arrhythmic episode may involve a polymorphic arrhythmia, such as ventricular fibrillation, that is not characterizable using a representative beat morphology. A therapy is delivered 178 to treat the unclassified tachyarrhythmia.

According to one scenario, illustrated in FIGS. 1A and 1C, arrhythmia classification may be performed by comparing the morphology of the cardiac beats associated with the arrhythmia episode to representative beat morphologies of various types of arrhythmia. The representative beat morphologies may be characterized by stored morphology templates. The morphology templates comprise features, samples, and/or morphological characteristics of cardiac beat signals representative of particular types of arrhythmia. An arrhythmic episode may be characterized as a particular type of arrhythmia, for example, a monomorphic VT (MVT), by determining that samples of the cardiac beats of the arrhythmic episode are correlated to the samples of a particular template. If the arrhythmic episode can be classified as the particular type of arrhythmia, then an appropriate therapy is delivered. For example, a therapy that was previously successful at terminating or mitigating the particular type of arrhythmia may be delivered to the patient.

In another scenario, illustrated by the flowcharts of FIGS. 1B and 1D, the type of arrhythmia experienced by the patient may not match with any previously stored representative beat morphology and the type of arrhythmic episode is thus unknown. If the tachyarrhythmia is a monomorphic arrhythmia, the type of arrhythmia may be characterizable by acquiring a morphology template representing the beat morphology of the type of arrhythmia. However, if the arrhythmia is polymorphic, a template representing a characteristic beat cannot be acquired.

A therapy may be delivered to treat the unclassified arrhythmia. If the arrhythmia is characterizable, then a first therapy may be delivered. If the arrhythmia is not characterizable, a different therapy may be delivered. Information related to the success of a therapy at treating an unclassified VT may be stored to enhance future treatment of an arrhythmia having similar characteristics.

In one example, a morphology template may be acquired for an unknown but characterizable arrhythmia. A therapy is delivered to treat the arrhythmia. The success of the therapy is determined. A therapy that is successful at treating the arrhythmia may be associated with the type of arrhythmia characterized by the acquired morphology template. If a subsequent episode of arrhythmia comprising cardiac beats that match the morphology template is detected, the episode may be treated using the successful therapy.

Figure 2:
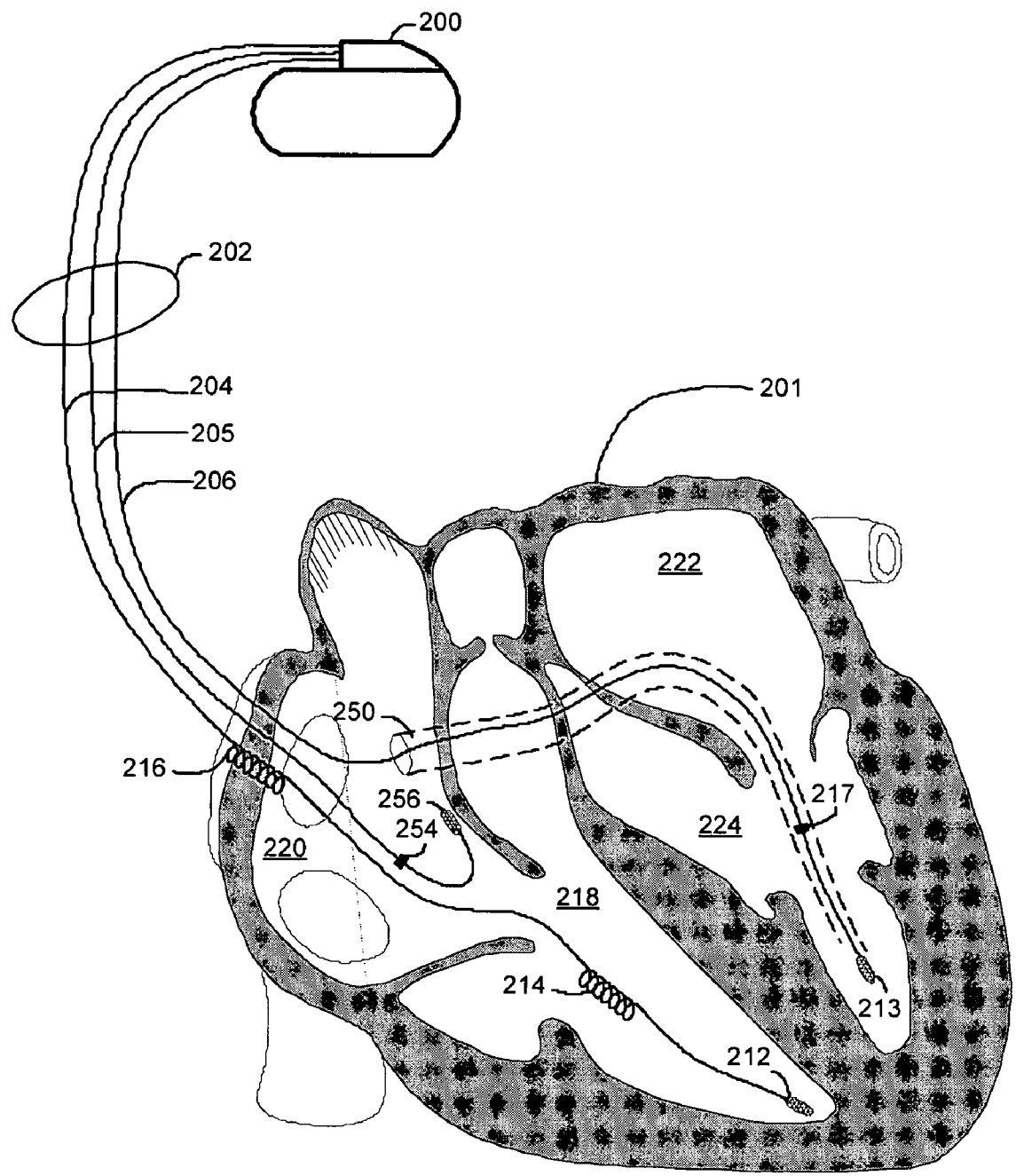
FIG. 2 is a partial view of an implantable medical device suitable for implementing arrhythmia classification and therapy delivery methods in accordance with embodiments of the invention.

FIG. 2 is a partial view of a cardiac rhythm management (CRM) device that may be used to implement arrhythmia classification and therapy methods in accordance with embodiments of the invention. Methods of the invention may be implemented in a variety of cardiac therapeutic and/or diagnostic devices including, for example, pacemakers, defibrillators, cardioverters, bi-ventricular pacemakers, and/or cardiac resynchronization devices, among others. The CRM device illustrated in FIG. 2 includes a pulse generator 200 electrically and physically coupled to intracardiac lead system 202. The intracardiac lead system 202 is implanted in a human body with portions of the intracardiac lead system 202 inserted into a heart 201. The intracardiac lead system 202 is used to detect electric cardiac signals produced by the heart 201 and to provide electrical energy to the heart 201 under predetermined conditions to treat cardiac arrhythmias.

The intracardiac lead system 202 includes one or more electrodes used for pacing, sensing, and/or defibrillation. In the particular embodiment shown in FIG. 2, the intracardiac lead system 202 includes a right ventricular lead system 204, a right atrial lead system 205, and a left ventricular lead system 206. In one embodiment, the right ventricular lead system 204 is configured as an integrated bipolar pace/shock lead.

The right ventricular lead system 204 includes an SVC-coil 216, an RV-coil 214, and an RV-tip electrode 212. The RV-coil 214, which may alternatively be configured as an RV-ring electrode, is spaced apart from the RV-tip electrode 212, which is a pacing electrode for the right ventricle.

The right atrial lead system 205 includes a RA-tip electrode 256 and an RA-ring electrode 254. The RA-tip 256 and RA-ring 254 electrodes may provide pacing pulses to the right atrium of the heart and may also be used to detect cardiac signals from the right atrium. In one configuration, the right atrial lead system 205 is configured as a J-lead.

In the configuration of FIG. 2, the intracardiac lead system 202 is shown positioned within the heart 201, with the right ventricular lead system 204 extending through the right atrium 220 and into the right ventricle 218. Typical locations for placement of the RV tip electrode are at the RV apex or the RV outflow tract.

In particular, the RV-tip electrode 212 and RV-coil electrode 214 are positioned at appropriate locations within the right ventricle 218. The SVC-coil 216 is positioned at an appropriate location within the right atrium chamber 220 of the heart 201 or a major vein leading to the right atrium chamber 220 of the heart 201. The RV-coil 214 and SVC-coil 216 depicted in FIG. 2 are defibrillation electrodes.

An LV distal electrode 213, and an LV proximal electrode 217 may be inserted through the coronary venous system and positioned adjacent to the left ventricle 224 of the heart 201. The LV proximal electrode 217 is spaced apart from the LV distal electrode, 213 which is a pacing electrode for the left ventricle. The LV distal 213 and LV proximal 217 electrodes may also be used for sensing the left ventricle.

The left ventricular lead system 206 includes endocardial pacing leads that are advanced through the superior vena cava (SVC), the right atrium 220, the ostium of the coronary sinus, and the coronary sinus 250 to locate the LV distal 213 and LV proximal 217 electrodes at appropriate locations adjacent to the left atrium and ventricle 222, 224, respectively.

The left ventricular lead 206 is guided into the right atrium 220 of the heart via the superior vena cava. From the right atrium 220, the left ventricular lead system 206 is deployed into the coronary sinus ostium, the opening of the coronary sinus 250. The lead system 206 is guided through the coronary sinus 250 to a coronary vein of the left ventricle 224. This vein is used as an access pathway for leads to reach the surfaces of the left atrium 222 and the left ventricle 224 which are not directly accessible from the right side of the heart. Lead placement for the left ventricular lead system 206 may be achieved via subclavian vein access and a preformed guiding catheter for insertion of the LV electrodes 213 and 217 adjacent the left ventricle 224. In one configuration, the left ventricular lead system 206 is implemented as a single-pass lead.

Figure 3:
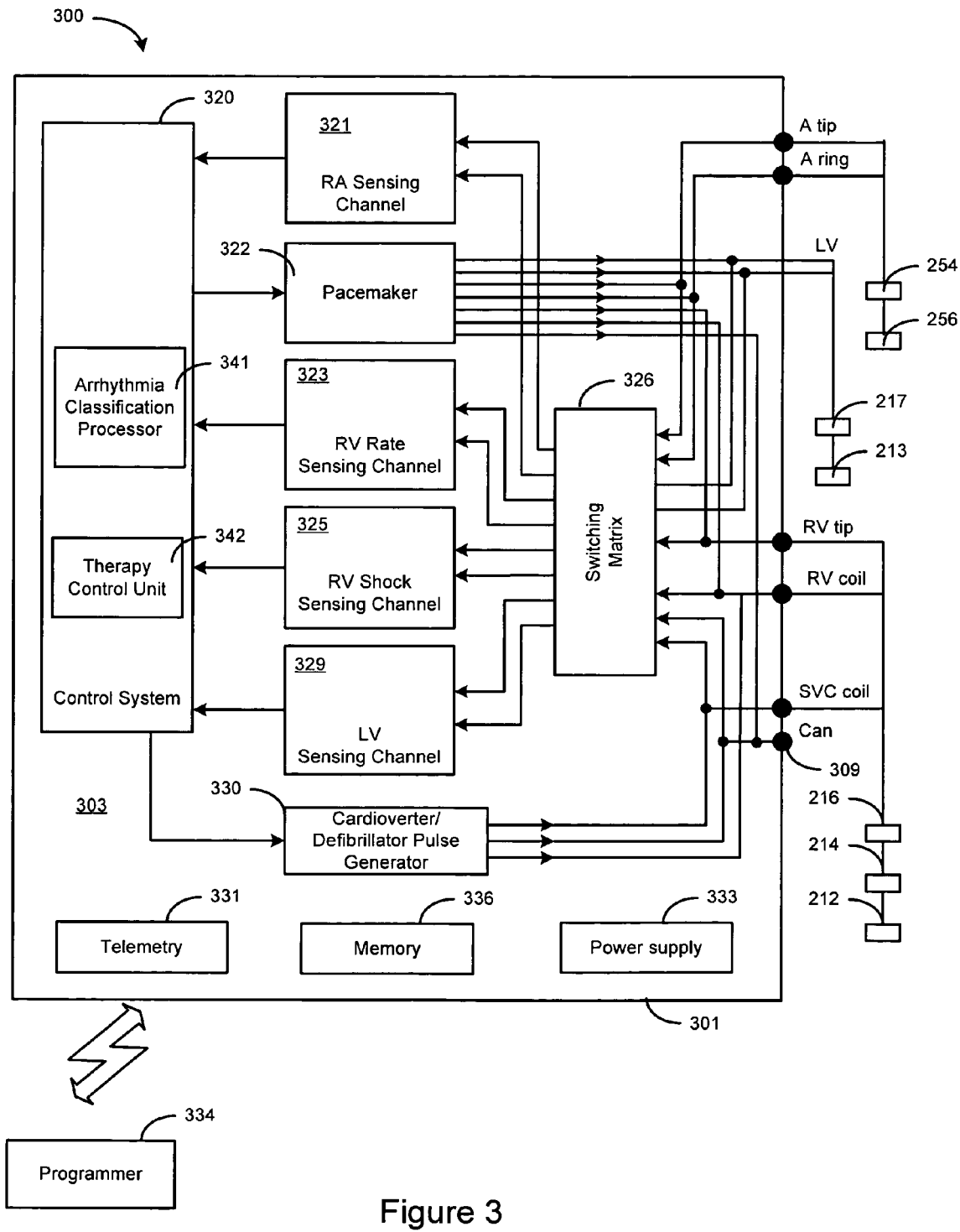
FIG. 3 is a block diagram of a cardiac rhythm management system in accordance with embodiments of the invention.

Referring now to FIG. 3, there is shown a block diagram of a cardiac rhythm management (CRM) device 300 suitable for implementing arrhythmia classification and therapy delivery in accordance with embodiments of the invention. FIG. 3 shows a CRM device 300 divided into functional blocks. It is understood by those skilled in the art that there exist many possible configurations in which these functional blocks can be arranged. The example depicted in FIG. 3 is one possible functional arrangement. Various functions of the CRM device 300 may be accomplished by hardware, software, or a combination of hardware and software.

The CRM device 300 includes components for sensing cardiac signals from a heart and delivering therapy, e.g., pacing pulses or defibrillation shocks, to the heart. The pulse generator (PG) 303 of the CRM device 300 may be encased and hermetically sealed in a housing 301 suitable for implanting in a human body. Power to the PG 303 is supplied by an electrochemical battery 333 that is enclosed within the housing 301. A connector block with lead terminals (not shown) is additionally attached to housing 301 to allow for the physical and electrical attachment of the intracardiac lead system conductors to the encased PG 303.

In one embodiment, the PG 303 is a programmable microprocessor-based system, including a control system 320, memory circuit 336, sensing circuitry 321, 323, 325, 329, pacemaker 322, and a cardioverter/defibrillator therapy circuit 330. Components of the PG 303 cooperatively perform operations involving arrhythmia classification and therapy delivery according to the approaches of the present invention. The control system 320 is responsible for arrhythmia detection, classification, and therapy control. The control system 320 may encompass various functional components, for example, an arrhythmia classification processor 341 and a therapy control unit 342.

A memory circuit 336 may be used to store historical records of sensed cardiac signals, including arrhythmic episodes, and/or information about therapy delivered to the patient. The memory circuit 336 may be used, for example, to store representative beat morphologies of various types of cardiac signals. Further associations between types of arrhythmia and therapies to treat the arrhythmia types may be stored in the memory 336.

The historical data stored in memory 336 may be used for various purposes, including diagnosis of patient diseases or disorders. Analysis of the historical data may be used and/or to adjust the operations of the CRM device 300. Data stored in the memory 336 may be transmitted to an external programmer unit 334 or other computing device, such as an advanced patient management system as needed or desired.

Telemetry circuitry 331 may be coupled to the PG 303 to allow the CRM device 300 to communicate with an external programmer unit 334 or other remote devices. In one embodiment, the telemetry circuitry 331 and the programmer unit 334 use a wire loop antenna and a radio frequency telemetric link to receive and transmit signals and data between the programmer unit 334 telemetry circuitry 331. In this manner, programming commands may be transferred to the control system 320 of the PG 303 from the programmer unit 334 during and after implant.

The pacemaker 322 may be used to deliver a series of electrical stimulations to the heart to regulate heart rhythm. In various embodiments, the pacemaker 322 may deliver pacing pulses to one or more of the right atrium, left atrium, right ventricle and the left ventricle. The heart may be paced to treat bradycardia, or to synchronize and/or coordinate contractions of the right and left ventricles. The pacemaker 322 may also provide tachyarrhythmia therapy in the form of anti-tachycardia pacing (ATP) pulses delivered to the heart. The ATP pulses may involve a series of timed paces of programmable width and amplitude that are implemented to interrupt a tachyarrhythmia episode. The ATP therapy may involve, for example, burst pacing at about 25 Hz to about 50 Hz. In various implementations, the pace-to-pace interval may have a variable or constant length.

In the embodiment depicted in FIG. 3, electrodes RA-tip 256, RA-ring 254, RV-tip 212, RV-coil 214, SVC coil 216, LV distal electrode 213, LV proximal electrode 217, and can 309 are coupled through a switching matrix 326 to various sensing circuits 321, 323, 325, 329. A right atrial sensing channel circuit 321 serves to detect and amplify electrical signals from the right atrium of the heart. For example, bipolar sensing in the right atrium may be implemented by sensing signals developed between the RA-tip 256 and RA-ring 254 electrodes. The switch matrix 326 is operated to couple the RA-tip 256 and RA-ring 254 electrodes to the RA sensing channel circuit 321 to effect bipolar sensing of right atrial signals. Alternatively, unipolar right atrial sensing may be accomplished by operating the switch matrix 326 to couple the RA-tip 256 and can 309 electrodes to the RA sensing channel circuit 321.

Cardiac signals sensed through the use of the RV-tip electrode 212 are right ventricular (RV) near-field signals and are referred to as RV rate channel signals herein. In the system shown in FIG. 2, the right ventricular lead is illustrated as an integrated pace/shock lead. In this configuration, bipolar rate channel sensing may be accomplished by operating the switch matrix 326 to couple the RV-tip 212 and the RV-coil electrodes 214 through the RV rate channel sensing circuitry 323. The rate channel signal may be detected, for example, as a voltage developed between the RV-tip 212 and the RV-coil 214 electrodes. The RV rate channel sensing circuitry 323 serves to sense and amplify the RV rate channel signal.

Unipolar RV sensing may be implemented, for example, by coupling the RV-tip 212 and can 309 electrodes to the RV rate channel sensing circuitry 323. In this configuration, the rate channel signal is detected as a voltage developed between the RV-tip 212 to can 309 sensing vector.

The RV lead system may also include an RV-ring electrode (not shown in FIG. 3) used for bipolar pacing and sensing. If an RV-ring electrode is included in the lead system, bipolar sensing may be accomplished by sensing a voltage developed between the RV-tip 212 and RV-ring (not shown) electrodes.

Far-field signals, such as cardiac signals sensed through use of one of the defibrillation coils or electrodes 214, 216 and the can 309, or using both of the defibrillation coils or electrodes 214, 216, are referred to as morphology or shock channel signals herein. The shock channel signal may be detected as a voltage developed between the RV-coil 214 to the can electrode 309, the RV-coil 214 to the SVC-coil 216, or the RV-coil 214 to the can electrode 309 shorted to the SVC-coil 216. The switch matrix 326 is operated to couple the desired shock channel sensing vector, e.g., RV-coil to can, to the RV shock channel sensing circuitry 325. The RV shock channel circuitry 325 serves to sense and amplify the shock channel signal.

The outputs of the switching matrix 326 may also be operated to couple selected combinations of the electrodes to LV sensing channel circuitry 329 for capture detection. For example, the LV proximal electrode 217 and the LV distal electrode 213 may be coupled though the switch matrix 326 to the LV sensing channel circuitry 329 to sense electrical signals from the left ventricle of the heart. The control system 320 receives signals from other components of the CRM device 300 and controls the operation of various CRM functions. The control system 320 serves as the control for a pacemaker 322 that delivers pacing pulses to one or more heart chambers. For example, pacing signals may be delivered to selected electrodes according to a preestablished pacing regimen under appropriate conditions.

Unipolar pacing of the right atrium may be accomplished, for example, by delivering pacing pulses between the RA-tip 256 and can 309 electrodes. Bipolar pacing of the right atrium may be accomplished by delivering pacing pulses between the RA-tip 256 and RA-ring 254 electrodes.

Right ventricular pacing may similarly be implemented using unipolar or bipolar configurations. Unipolar RV pacing involves, for example, pacing pulses delivered between the RV-tip 212 to can 309 electrodes. Bipolar pacing involves, for example, delivery of pacing pulses between the RV-tip 212 to RV-coil 214 electrodes. If an RV-ring electrode is present, bipolar pacing may be accomplished by delivering the pacing pulses to the RV-tip 212 and RV-ring (not shown) electrodes.

Left ventricular pacing may be implemented using unipolar or bipolar configurations. Unipolar LV pacing may include, for example, pacing pulses delivered between the LV distal electrode 213 and the can 309. Alternatively, bipolar LV pacing may be accomplished by delivering the pacing pulses using the LV distal electrode 213 and the LV proximal electrode 217.

The CRM device 300 includes an arrhythmia classification processor 341 configured to classify a variety of arrhythmias, including types of monomorphic tachyarrhythmia. The arrhythmia classification processor 341 may detect and/or classify arrhythmia based on morphological analysis of cardiac signals. The morphological analysis may be performed, for example, by comparing detected atrial or ventricular cardiac beats to stored templates characterizing arrhythmic beats and/or normally conducted beats.

In one implementation, discrimination between supraventricular tachyarrhythmia (SVT) and ventricular tachyarrhythmia (VT) may be accomplished by comparing cardiac beats to a template characterizing the patient's normal supraventricular rhythm (SVR). If the cardiac beats are consistent with the SVR template, then the tachyarrhythmia is determined to be supraventricular in origin. In another example, the arrhythmia classification processor 341 may classify an arrhythmia by comparing the morphology of cardiac beats to templates characterizing ventricular tachycardia, atrial fibrillation and/or atrial flutter. Other arrhythmia detection and/or classification methodologies, e.g., rate based and pattern based arrhythmia detection, are known in the art and may also be implemented by the arrhythmia classification processor 341.

If an arrhythmia is classified by the arrhythmia classification processor 341, the control system 320 may communicate with the cardioverter/defibrillator pulse generator 330 or the pacemaker 322 to initiate an appropriate therapy, such as ATP, cardioversion and/or defibrillation shocks, to mitigate or terminate the arrhythmia. The therapy control unit 342 may associate one or more therapies with types of arrhythmias. For example, if a therapy proves to be successful at treating a particular type of arrhythmia, the therapy control unit associates the therapy with the type of arrhythmia. If the particular type of arrhythmia is subsequently detected, the therapy control unit selects the previously successful therapy to be delivered to the patient.

The therapies delivered to treat the arrhythmia may be delivered in a selected order. The order of therapy delivery may involve delivering a more successful therapy first, followed by other therapies.

Figure 4:
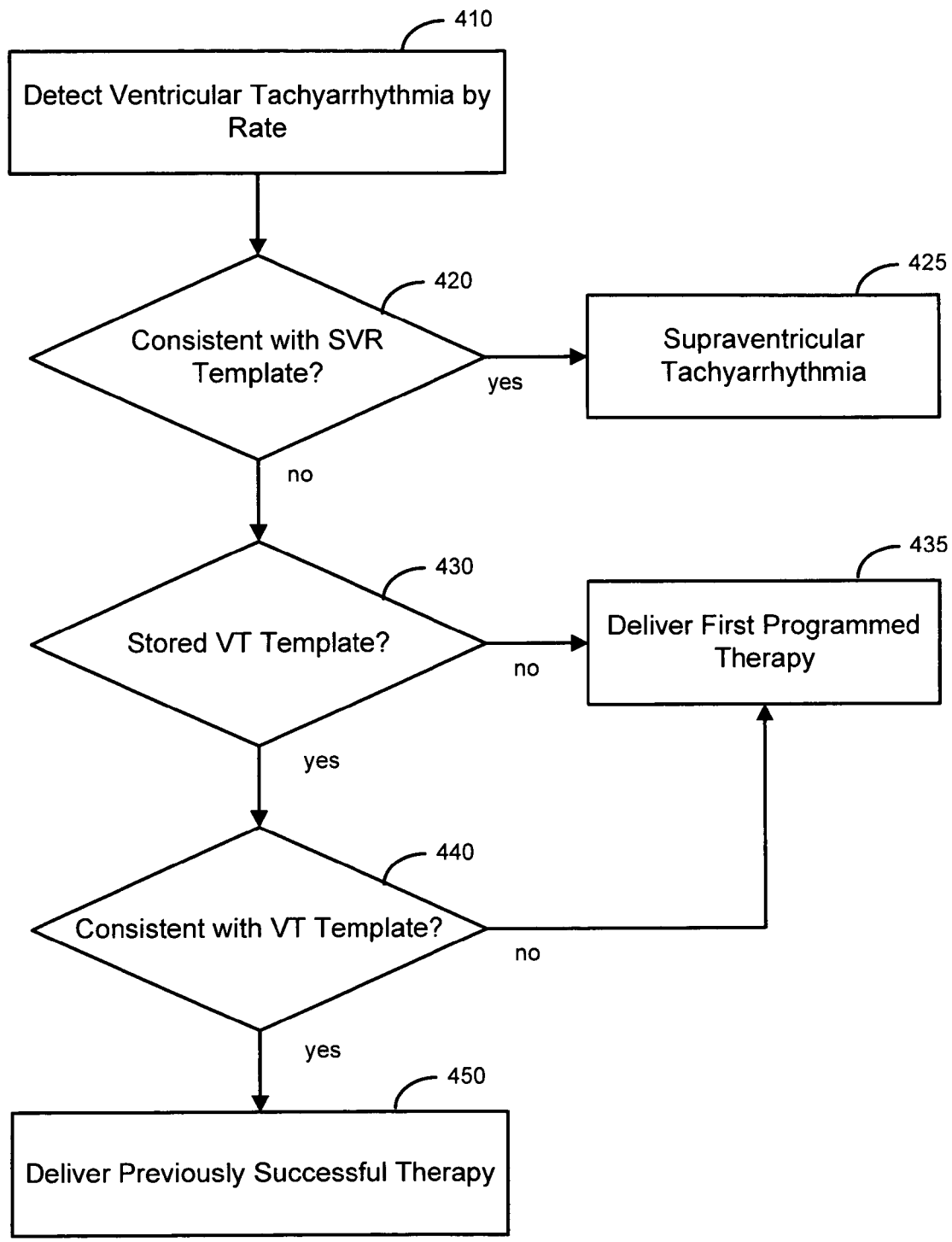
FIG. 4 is a flowchart illustrating a method for classifying arrhythmia and delivering cardiac therapy to a patient in accordance with embodiments of the invention.

FIG. 4 is a flowchart illustrating a method for delivering cardiac therapy to a patient in accordance with embodiments of the invention. An arrhythmia is detected 410 based on heart rate. For example, tachyarrhythmia may initially be detected based on ventricular rate by evaluating the patient's V-V intervals. If the system detects a ventricular rate above a threshold, then the system flags the episode as a tachyarrhythmic episode. The tachyarrhythmic rate may be categorized as a relatively fast, medium, or slow tachyarrhythmia based on a number or percentage of intervals, e.g., V-V intervals, that fall within specified ranges for relatively fast, medium, or slow tachyarrhythmia.

After the tachyarrhythmia is initially detected 410 based on rate, a morphological analysis process may be implemented to further classify the type of tachyarrhythmia. In one implementation, the morphology of one or more cardiac beats of the tachyarrhythmic episode is compared to a morphology template characterizing the patient's supraventricular rhythm (SVR). Various methods of acquiring an SVR template are described in commonly owned U.S. patent application Ser. No. 09/845,987, filed Apr. 30, 2001, commonly owned U.S. patent application Ser. No. 10/105,875, filed Mar. 25, 2002, and commonly owned U.S. Pat. No. 6,449,503 which are incorporated herein by reference in their respective entireties.

If the one or more cardiac beats are consistent with 420 the SVR template, then the tachyarrhythmia is classified 425 as a supraventricular tachyarrhythmia (SVT). In one embodiment, the tachyarrhythmia is classified as an SVT if x out of y beats are consistent with the SVR template. For example, the tachyarrhythmia may be classified as an SVT if at least about 3 out of about 10 beats are consistent with the SVR template. If the tachyarrhythmia is classified as SVT, therapy may not be indicated.

If the morphology of the cardiac beats is not consistent 420 with the SVR template, then the morphology of the cardiac beats may be compared to previously stored VT templates. If the cardiac beat morphology is consistent with 440 a VT morphology template, then a therapy that was previously successful at treating the VT is delivered 450. If the cardiac beat morphology is not consistent with 440 a VT template, or if there are no previously stored 430 VT templates, then the system delivers 435 a programmed therapy.

According to embodiments of present invention, VT templates may be acquired and/or updated and made available for classification of detected arrhythmic episodes. Templates characterizing VT rhythms can only be updated when additional similar VT episodes occur. Templates associated with types of arrhythmia can be acquired or updated automatically or manually. For example, a CRM device may automatically attempt to acquire a VT template upon detection of a rapid ventricular rate that is determined to be ventricular in origin and for which no stored template exists. Alternatively, the physician may identify a VT stored in memory as a past episode and request the implantable system to form a VT template from episode records. In one scenario, the physician may identify a new type of VT and may request that a new VT template be formed. In another scenario, the physician may identify a misclassified VT and request the implantable system to form a VT template for the misclassified VT. Accurate template formation for a particular type of VT is dependent on the presentation of a consistent beat-to-beat morphology. However, if the cardiac rhythm is disorganized, such as in a polymorphic VT, determination of a representative beat morphology that characterizes the rhythm may not be possible.

A particular therapy may be selected to treat a particular type of VT. For example, if a therapy is determined to have successfully mitigated or terminated a particular type of VT, information identifying and associating the previously successful therapy with the particular type of VT may be stored in the CRM device memory and utilized by the therapy control unit. If a subsequent episode of the particular type of VT is detected, the previously successful therapy may be selected to treat the particular type of VT. Identification of a therapy that will be used for treatment of a particular type of VT may be performed automatically by the CRM device or manually based on electrogram (EGM) data.

Figure 5A:
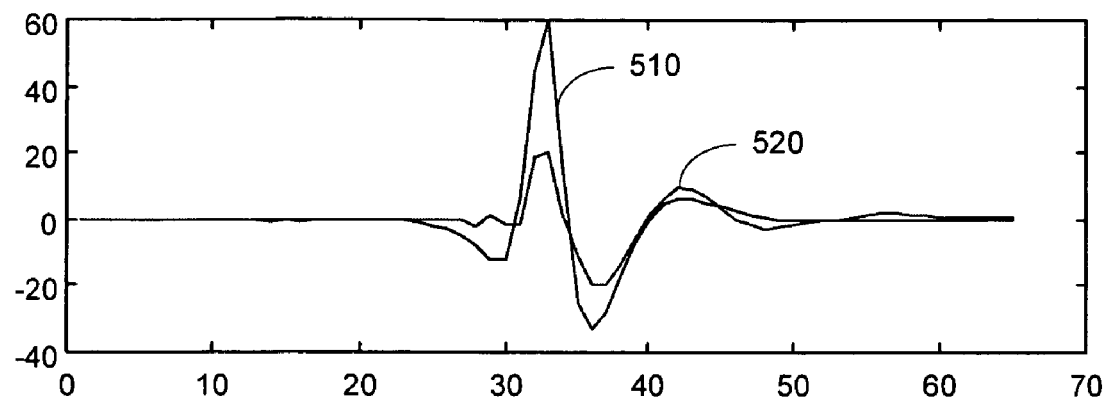
FIGS. 5A and 5B are graphs illustrating the use of rate and shock channel signals for arrhythmia classification in accordance with embodiments of the invention.
Figure 5B:
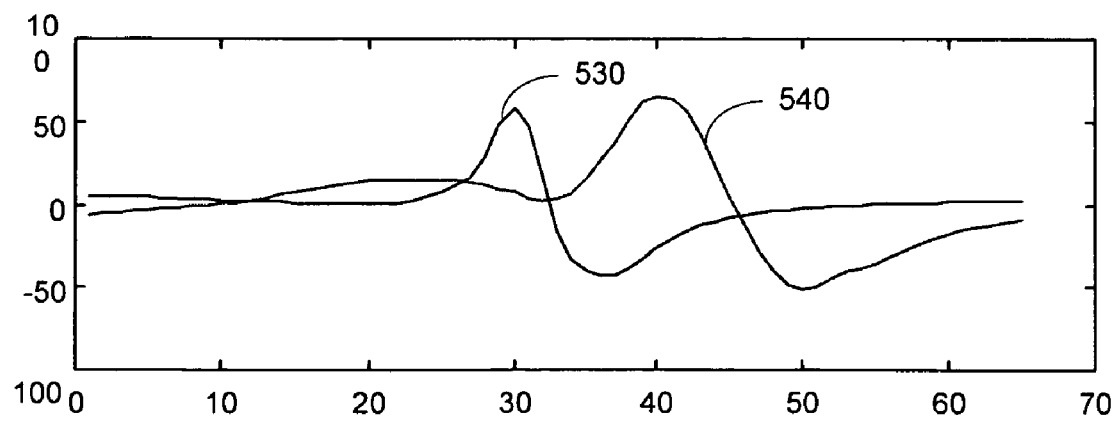

The representative beat morphologies of a number of types of VT may be characterized using morphology templates. In one implementation, template acquisition may be accomplished using a two channel approach. Cardiac beats are sensed on a rate channel and a shock channel. In this example, a feature of the rate channel signal, e.g., the rate channel R-wave peak, may be used to align the shock channels of multiple cardiac beats. Samples or features of the aligned shock channel signals are used to form the template. FIGS. 5A and 5B illustrate the process of rate and shock channel alignment. FIG. 5A illustrates aligned rate channel signals of a normal sinus rhythm (NSR) beat 510 and a VT beat 520, respectively. FIG. 5B illustrates the aligned shock channel signals of the NSR beat 530 and the VT beat 540.

Template formation may involve applying one or more initial criteria to a cardiac beat or a series of cardiac beats before a cardiac beat is used for template formation. For example, the initial criteria may involve meeting various duration, stability, rate, onset, and/or other arrhythmia discrimination criteria prior to using a cardiac beat as a template beat. For example, prior to using a beat as a template beat, the duration of the cardiac rhythm, the rate of the cardiac rhythm, the stability of the cardiac rhythm and/or the onset of the cardiac rhythm may be respectively compared to duration, rate, stability, and onset criteria.

For example, the cardiac rhythm stability may be evaluated by evaluating R-R intervals. A stability analysis algorithm calculates R-R interval differences. The rhythm stability is evaluated by comparing the current average difference to a programmed stability threshold. If the rhythm does not meet stability criteria, then acquisition of a template may not be desirable because unstable rhythms are presumed to be less morphologically consistent than stable rhythms. In this scenario, the unstable rhythm is classified as an unknown rhythm.

Figure 6:
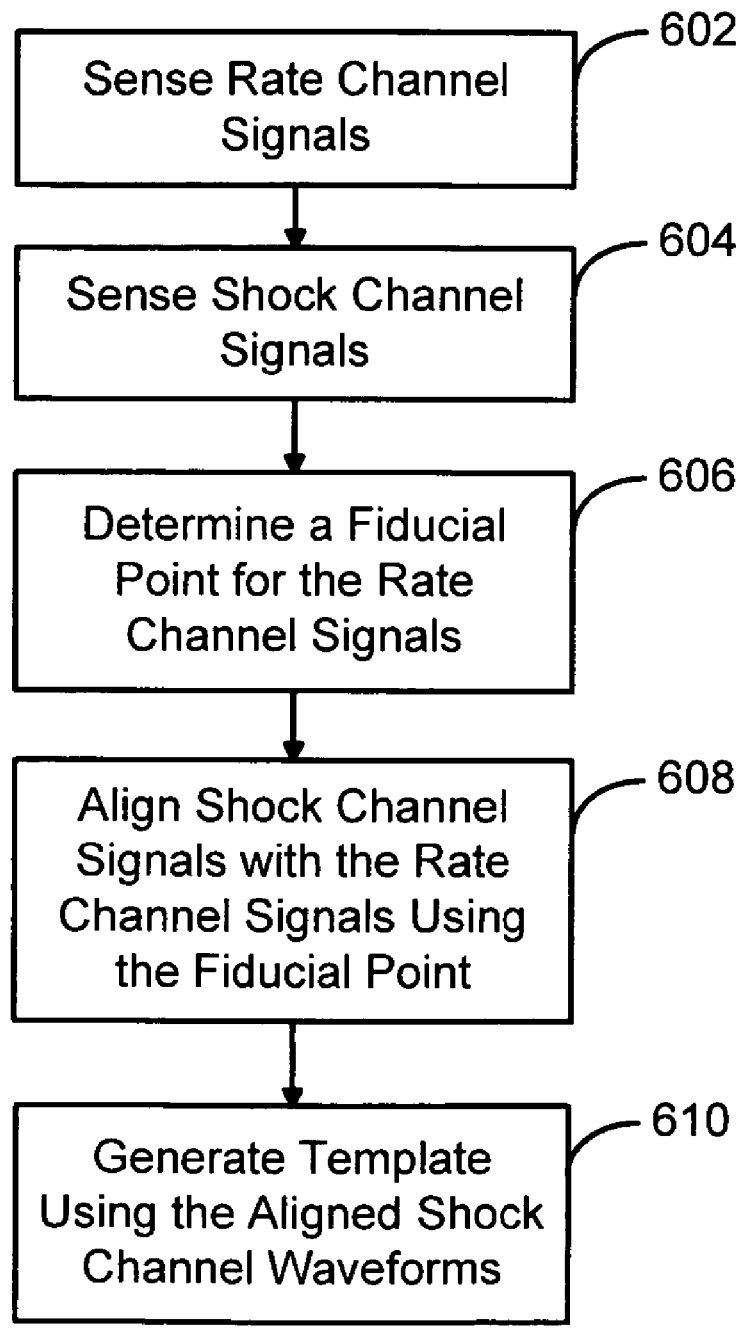
FIG. 6 is a flowchart illustrating a method of forming a template that may be used for arrhythmia classification in accordance with embodiments of the invention.

Onset criteria may involve, for example, evaluation of how quickly a particular rhythm occurs. An onset algorithm measures the rate of transition in a rhythm from a first rate to a second rate. If the onset of a cardiac rhythm occurs at a rate that is inconsistent with a threshold rate, then the rhythm may not be suitable for template generation. For example, if the rhythm onset is gradual, the rhythm is likely to be sinus tachycardia and a VT template is not needed. FIG. 6 provides a more detailed illustration of the processes associated with forming a template in accordance with embodiments of the invention.

A template may be formed by combining one or more beats, wherein the combination of beats represents one beat of a particular rhythm, such as a monomorphic VT rhythm. Rate channel signals and shock channel signals of one or more cardiac beats representative of the cardiac rhythm being characterized are sensed 602, 604. The peaks of the rate channel signals are identified 606 as fiducial points. The rate channel fiducial points are used to align 608 the corresponding shock channel signals of each template beat. The aligned shock channel signals may be combined, for example, by averaging the aligned signals sample by sample, or by other methods.

In one implementation, the template may comprise all samples of the average shock channel waveform. In another implementation, a selected set of samples of the average shock channel waveform may be extracted and used to form the template. In yet another implementation, morphological characteristics of the cardiac beats used to form the template may be used as the template. For example, the template may comprise one or more features such as a QRS width, an amplitude, peak timing, and/or other morphological features of the rate channel, shock channel, or combinations thereof.

As previously discussed, the representative beat morphology of various types of VT may be acquired manually. Manual identification of representative beat morphology may be accomplished by a physician or other person. For example, the patient's physician may examine stored electrogram (EGM) data acquired by the CRM device or another device to determine morphological features characterizing the representative beat morphology of monomorphic VT episodes. The morphological features may be input to the CRM device for use in identifying subsequent episodes of the type of VT.

Therapies may also be selected and associated with VT types through a manual process. A physician or other person may identify therapies that are likely to be, or have been, most successful at treating various types of VT. Identification of the therapies may be accomplished by examining EGM data corresponding to previous VT episodes and the result of treatment of the VT episodes. A therapy that was previously successful at treating a particular type of VT may be identified by the physician. Knowledge of an effective therapy or therapies may be acquired from a patient's previous device and/or during experience gained during an electrophysiological (EP) study. An association between the particular type of VT and the successful therapy may be input to the CRM device and stored in memory. When the CRM device detects a subsequent episode of the particular type of VT, the previously successful therapy is delivered.

Figure 7A:
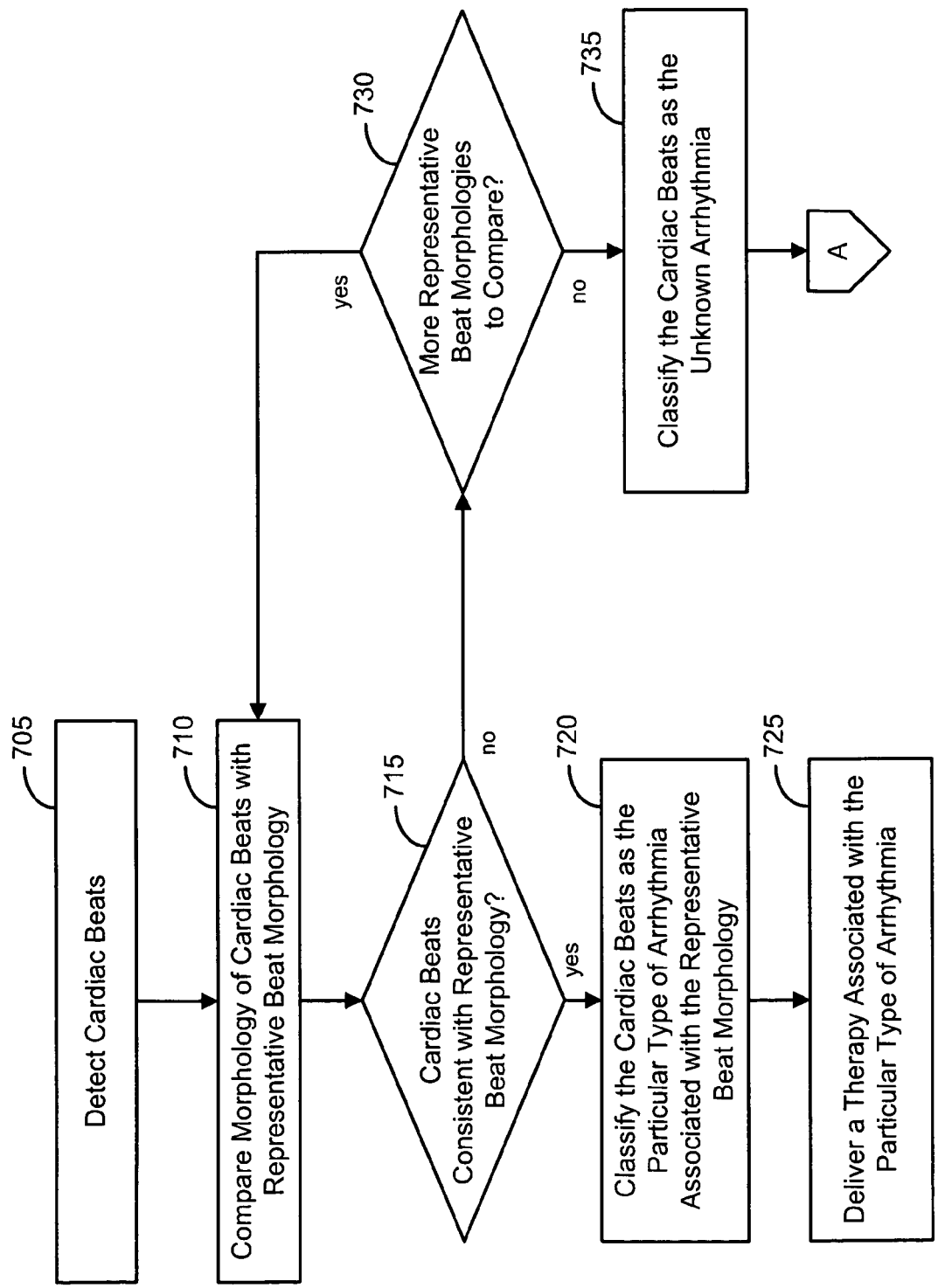
FIGS. 7A and 7B are flowcharts illustrating a method of providing therapy for characterizable and uncharacterizable arrhythmic episodes in accordance with embodiments of the invention.
Figure 7B:
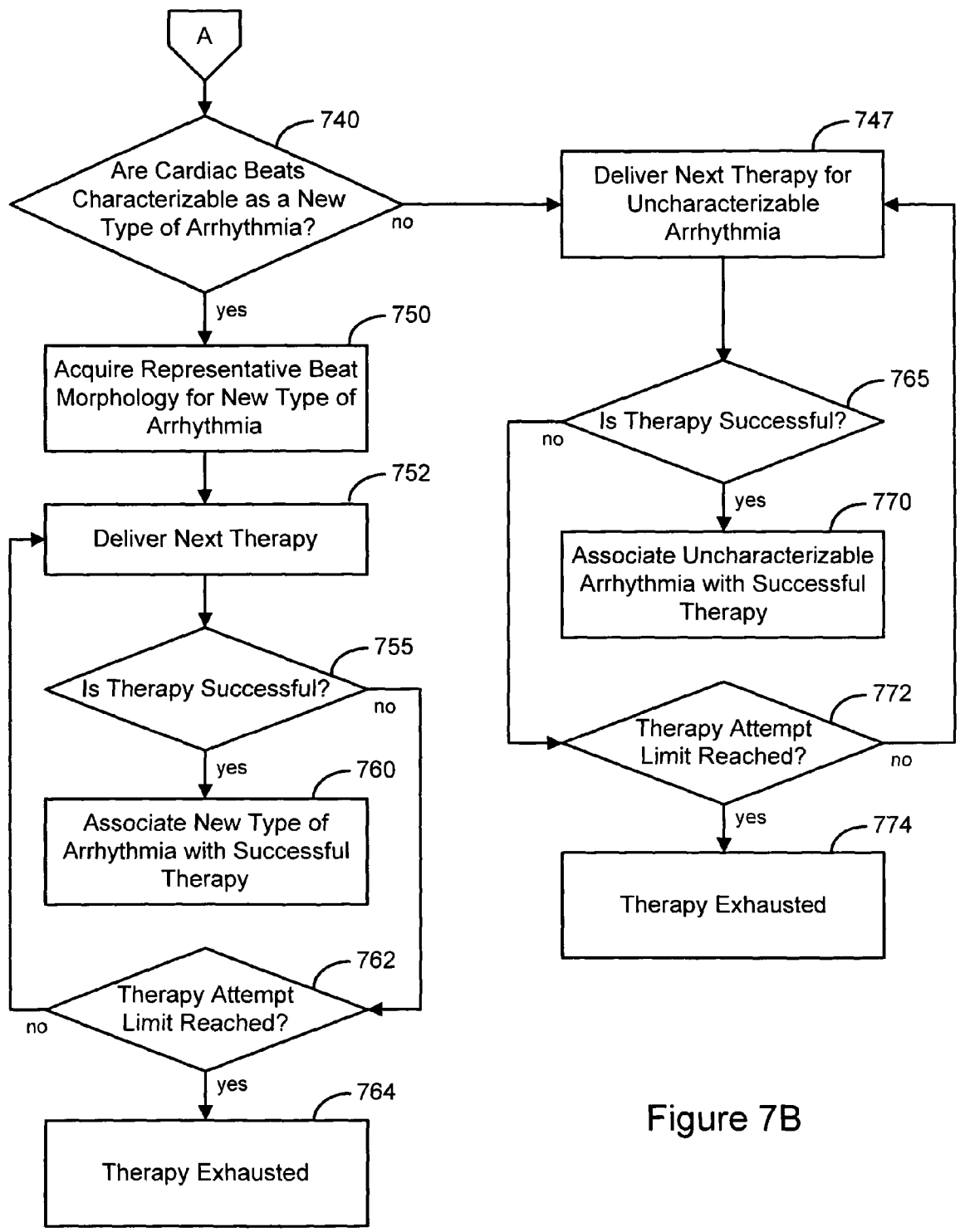

FIGS. 7A and 7B illustrate a flowchart of a method for delivering therapy to a patient based on recognition of particular types of arrhythmia according to embodiments of the invention. Representative beat morphologies associated with types of arrhythmia may be acquired and stored for use in classification of subsequent arrhythmic episodes. One or more particular therapies may be associated with one or more types of arrhythmia and may be the first therapy used to treat the VT types with which it is associated. In one implementation, additional therapies may be delivered following delivery of the first therapy.

Turning to the flowchart of FIG. 7A, cardiac beats of an arrhythmic episode are detected 705. The morphologies of the cardiac beats are compared 710 to a representative beat morphology associated with a type of arrhythmia. In one example, the representative beat morphologies are compared to the cardiac beats in a specified order. For example, a representative beat morphology of a more frequently detected type of arrhythmia may be compared to the cardiac beats before other representative beat morphologies are compared. If the morphologies of the cardiac beats are consistent with 715 a representative beat morphology, then the arrhythmic episode is classified 720 as the particular type of arrhythmia associated with the representative beat morphology. A therapy associated with the particular type of arrhythmia is delivered 725.

If the morphologies of the cardiac beats are not consistent 715 with the particular type of VT, and there are more representative beat morphologies to compare 730, then the cardiac beat morphologies are compared 710 to the representative beat morphology of the next type of arrhythmia. If all the stored representative beat morphologies are checked 730 and the morphologies of the cardiac beats are not consistent with any of the stored representative beat morphologies, then the arrhythmic episode is classified 735 as an unknown or unclassified type of arrhythmia.

The process of characterizing an unknown type of arrhythmia and identifying a successful therapy continues in FIG. 7B. The morphologies of the cardiac beats of the arrhythmic episode may be characterizable 740 if the arrhythmia comprises a monomorphic tachyarrhythmia having a consistent morphology. However, if the morphologies of the cardiac beats of the arrhythmic episode are uncharacterizable, then the arrhythmic episode is classified as an uncharacterizable arrhythmia, e.g., a polymorphic or multi-morphology VT episode, then a therapy selected for uncharacterizable ventricular tachyarrhythmia may be delivered 747. If the therapy successfully treats 765 the uncharacterizable arrhythmia, then the successful therapy may be associated 770 with uncharacterizable arrhythmia.

If the therapy is not successful 765 at treating the uncharacterizable arrhythmia, then additional therapies may be tried 747. The successful therapy, if any, may be associated 770 with uncharacterizable arrhythmia. The successful therapy may then be selected and used to treat subsequently detected episodes of uncharacterizable arrhythmia. A representative set of cardiac therapies for uncharacterizable arrhythmia such as polymorphic VT or VF may include, for example, burst, ramp, or scan ATP pacing, cardioversion shocks, and defibrillation shocks.

Association of a particular therapy with an uncharacterizable arrhythmia may not always be desirable. For example, ATP may terminate a polymorphic VT, but would be inappropriate for torsade de pointes. Thus, this feature may be disabled on a case by case basis depending on the types of arrhythmias the patient is expected to experience.

The ATP therapy schemes and redetection time should be brief before advancing to therapeutic shock due to minimize duration of any hemodynamic instability associated with the polymorphic rhythm.

If the cardiac beat morphology of the arrhythmia is characterizable 740, then a representative beat morphology is acquired 750 and stored for the new type of arrhythmia. A therapy is delivered 752 to treat the new type of VT. If the first delivered therapy is successful 755 then the successful therapy is associated 760 with the new type of arrhythmia, e.g., an arrhythmia for which a representative morphology had not been previously acquired. If the first delivered therapy is not successful 755, then a next available therapy is delivered 752. The successful therapy, if any, is associated 760 with new type of arrhythmia. The successful therapy may then be selected and used to treat subsequently detected episodes of the new type of arrhythmia.

Figure 7C:
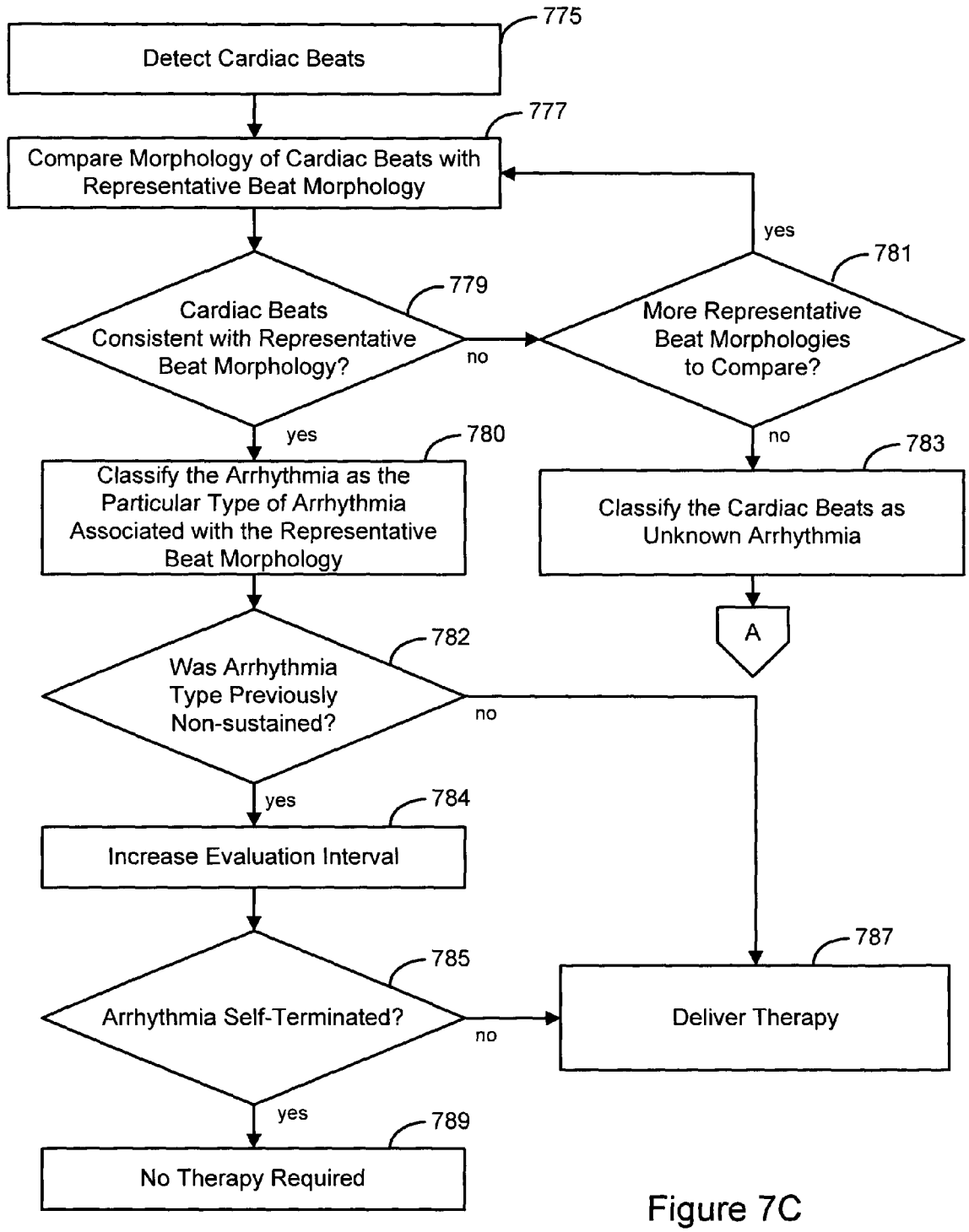
FIG. 7C is a flowchart illustrating a method of modifying arrhythmia discrimination parameters in accordance with embodiments of the invention.

In attempting to acquire templates and/or classify the types of arrhythmia, the CRM device may alter one or more of the arrhythmia discrimination parameters, such as the duration interval or number of cardiac beats used for identifying the rhythm. In one example, the CRM device may learn that certain types of monomorphic arrhythmia or other rhythms may be non-sustained. If a particular type of rhythm is identified as a previously non-sustained arrhythmia type, the device may respond by increasing the duration that an episode is evaluated to allow the arrhythmia episode to self-terminate. For example, a non-sustained VT may last less than about 5 to about 20 seconds, for example. A flowchart illustrating this process is provided in FIG. 7C.

Cardiac beats of an arrhythmic episode are detected 775. The morphologies of the cardiac beats are compared 777 to a representative beat morphology associated with a particular type of arrhythmia. If the morphologies of the cardiac beats are consistent with 779 the representative beat morphology, then the arrhythmic episode is classified 780 as the particular type of arrhythmia.

If the cardiac beats are not consistent with the representative beat morphology 779 and there are no more representative beats morphologies to compare 781, the cardiac beats are classified 783 as an unknown arrhythmia and the process continues as in FIG. 7B.

If the particular type of arrhythmia was previously a sustained arrhythmia 782, then the therapy associated with the particular type of arrhythmia is delivered 787. However, if the particular type of arrhythmia was previously a non-sustained arrhythmia 782, then the length of time that the arrhythmia is evaluated may be increased 784. After the increased evaluation time, the rhythm is rechecked. If the arrhythmia self-terminated 785, then no therapy is required 789. If the arrhythmia continues 785, then the therapy associated with the particular type of arrhythmia is delivered 787. The type of arrhythmia may be reclassified during or following the increased evaluation interval. In this situation, a therapy associated with the reclassified VT is delivered. The system may update information stored about the arrhythmia, for example whether the arrhythmia was sustained or non-sustained, the duration of the non-sustained rhythms, and/or whether the arrhythmia was reclassified during the increased evaluation period.

Figure 8A:
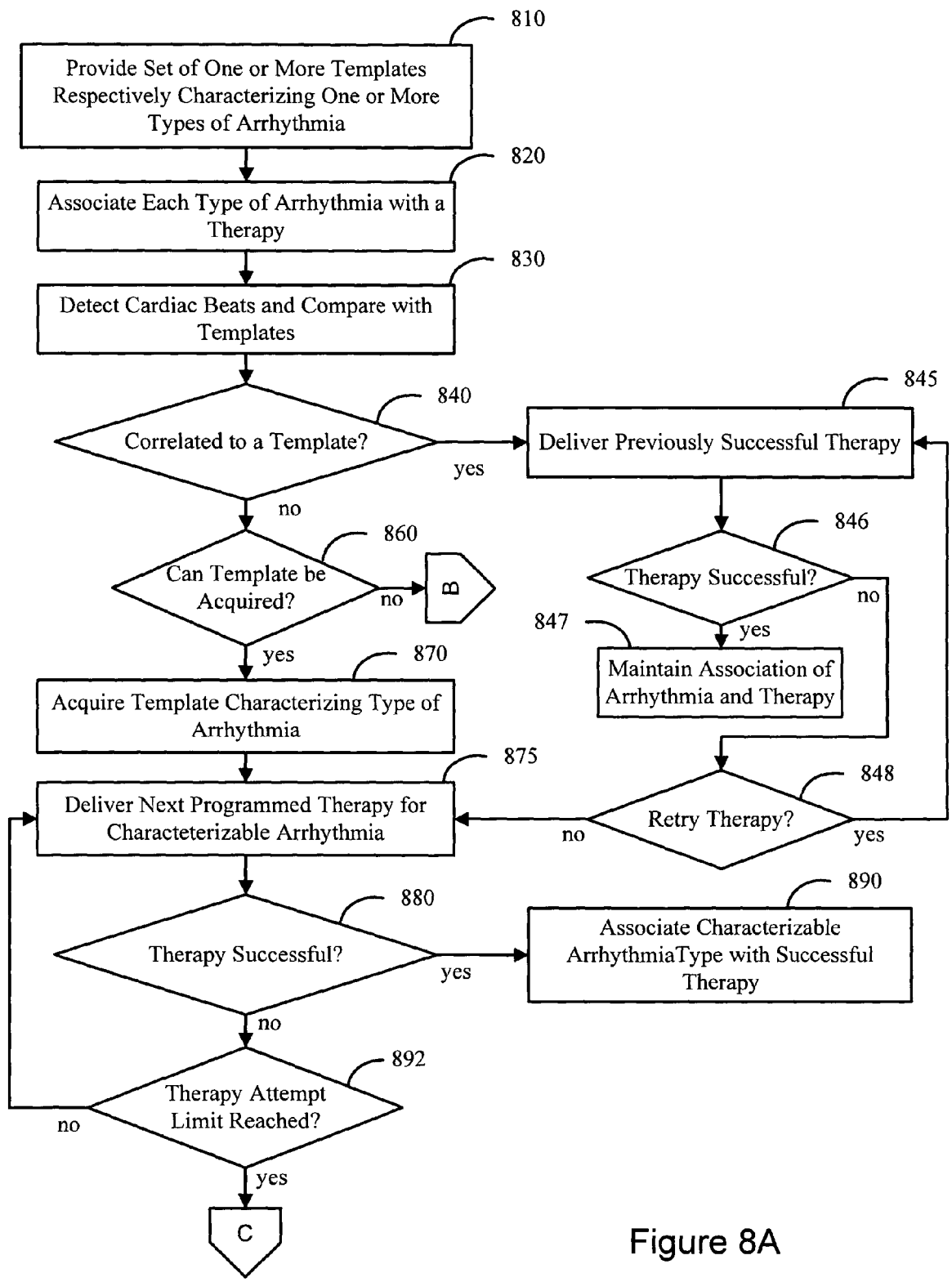
FIGS. 8A and 8B are flowcharts illustrating a method of associating a successful therapy with a type of arrhythmia in accordance with embodiments of the invention.
Figure 8B:
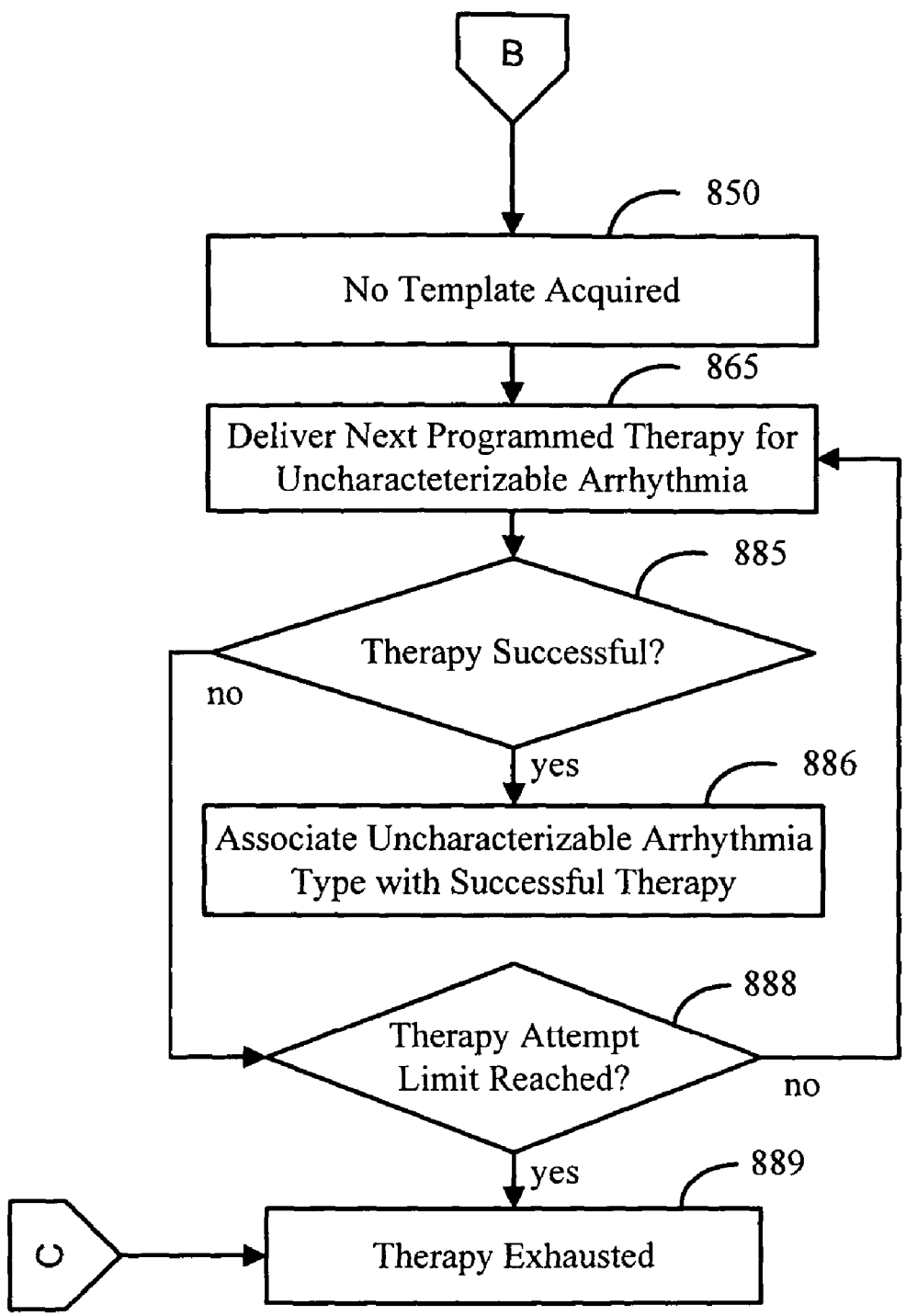

FIGS. 8A and 8B are flowcharts illustrating a process of using morphology templates to identify types of arrhythmia and to select an appropriate therapy. Morphology templates characterizing one or more types of identified arrhythmia are provided 810, e.g., stored in memory. In one implementation, each morphology template may be associated 820 with a particular type of arrhythmia. Each particular type of arrhythmia may be associated with a therapy that is used to treat the particular type of arrhythmia. A therapy may be associated with multiple types of arrhythmia.

Cardiac beats of an arrhythmic episode are detected and compared 830 to templates characterizing the various types of identified arrhythmias. The order in which the stored templates are compared to the cardiac beats may vary. In one implementation, the order in which the arrhythmia templates are compared to the cardiac beats is determined based on the frequency of occurrence of the types of arrhythmia. For example, the cardiac beats of an arrhythmic episode may be compared to a template characterizing a more frequently occurring type of arrhythmia before the cardiac beats are compared to a template characterizing a less frequently occurring type of arrhythmia. The number of templates compared to the cardiac beat morphology may be limited to a predetermined number of templates.

If the morphology of the detected cardiac beats is correlated 840 to a stored arrhythmia template, a therapy associated with the type of arrhythmia is delivered 845. In a preferred implementation, the therapy associated with the type of arrhythmia comprises a previously successful therapy.

If the previously successful therapy is attempted and again successfully terminates 846 the arrhythmia, the association between the type of arrhythmia and the therapy is maintained 847. If the previously successful therapy does not terminate 846 the arrhythmia, then the therapy may be retried 848 for a predetermined number of times, for example, about 2 times. If the previously successful therapy does not successfully terminate 846 the arrhythmia after being retried 848 the predetermined number of times, then the next programmed therapy is delivered 875.

A number of therapies may be associated with a type of arrhythmia. The therapies delivered to treat the type of arrhythmia may be delivered in a particular order, for example, in the order of a therapy success rating. For example, a therapy determined to be more successful at treating the type of arrhythmia may be delivered first, followed by delivery of the next most successful therapy if the more successful therapy does not mitigate the arrhythmia, and so forth. The therapy success rating for a particular therapy may be determined, for example, based on a percentage of successful treatments using the particular therapy. Thus, if a therapy was previously successful, but becomes less successful at treating the type of arrhythmia, then the previously successful therapy may be replaced by other, more successful therapies. Another example of determining the order of therapies delivered to treat a type of arrhythmia may involve first delivering the one or more therapies that were most recently successful at treating the arrhythmia.

If the morphology of the detected cardiac beats is not correlated 840 to a stored arrhythmia template, an arrhythmia template characterizing the type of arrhythmia may be acquired 870, if possible 860. In one implementation, a morphology template may be acquired 870 by a quick template formation method using about 8 to about 10 cardiac beats. A quick template formation method is described in connection with generation of an SVR template in commonly owned U.S. patent application Ser. No. 10/105,875, previously incorporated by reference herein.

In one embodiment, illustrated in FIG. 8A, a template is acquired 870, if possible 860, and a therapy is delivered 875 to treat the arrhythmia. In other embodiments, a template may be acquired for previously unknown arrhythmias without the delivery of therapy. If the arrhythmia is uncharacterizable 860, then no template is acquired 850 (FIG. 8B) and therapy to treat the uncharacterizable arrhythmia may be delivered 865. If the therapy to treat the uncharacterizable arrhythmia is successful 885, then the therapy may be associated with uncharacterizable arrhythmia 886 as a successful therapy. Otherwise, the next programmed therapy may be delivered 865. The system may attempt 888 a predetermined number of therapies before therapy attempts are exhausted 889. Information linking a successful therapy with uncharacterizable arrhythmia may be stored in the device memory. The successful therapy may be used to treat subsequent episodes of uncharacterizable arrhythmia as a first selected therapy.

If a template representing the type of arrhythmia was acquired 870 (FIG. 8A) and the therapy delivered 875 was successful 880, then information linking the successful therapy to the arrhythmia is stored 890. Otherwise, the next programmed therapy may be delivered 875. The system may attempt 892 a predetermined number of therapies before therapy attempts are exhausted 889.

Memory available to store templates associated with the arrhythmias may be limited. Thus, templates may be deleted from memory if the arrhythmias they represent have not been detected for a period of time, thus freeing up memory space for more recently detected arrhythmia templates. In one scenario, a newly acquired template may replace a template representing a rhythm that has not been detected for the longest period of time. Further, a manual process for deleting old and/or spurious templates may be used, wherein a physician deletes templates from memory.

Figure 9:
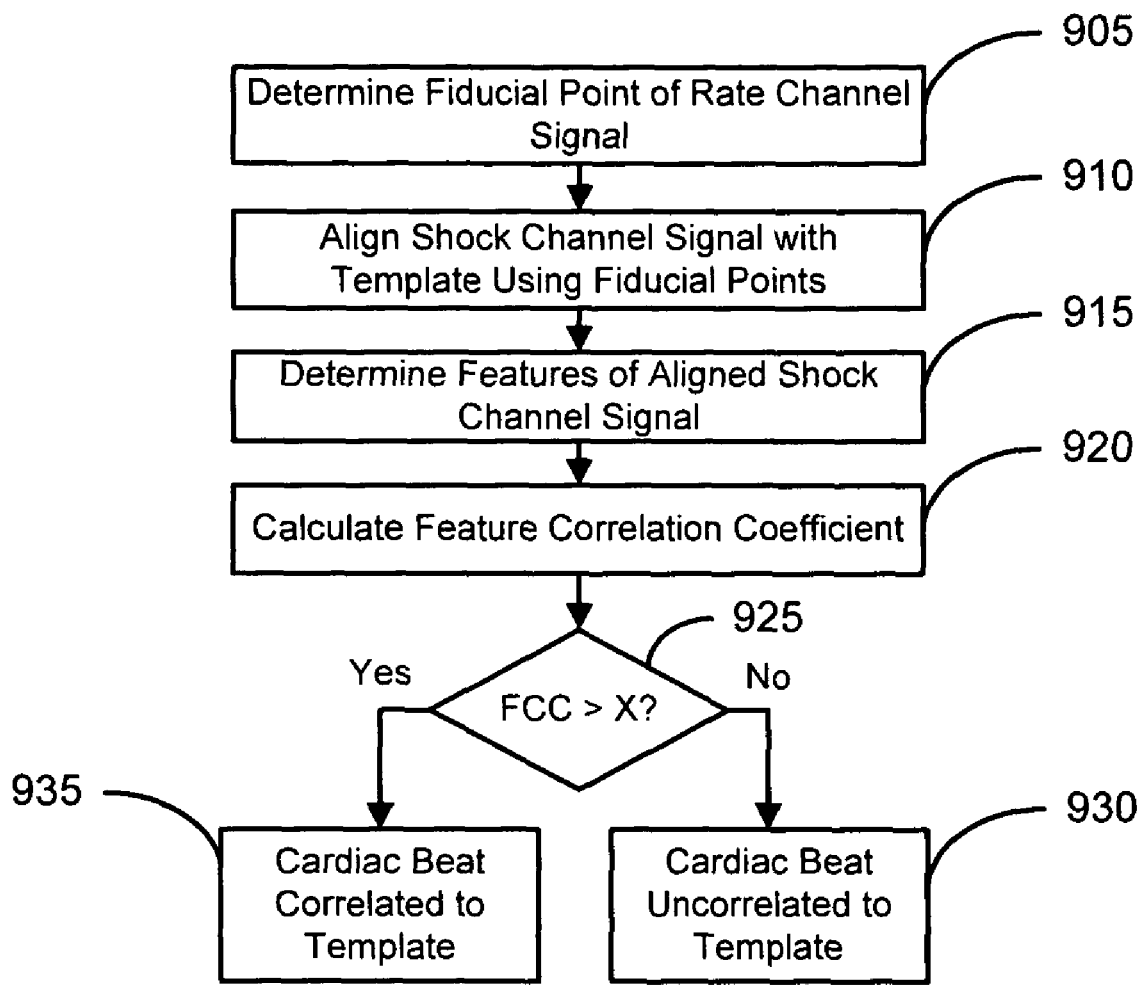
FIG. 9 illustrates a method of determining if a cardiac beat is correlated to a template in accordance with embodiments of the invention.

FIG. 9 provides a more detailed illustration of various steps associated with determining if a cardiac beat is correlated to a template in accordance with embodiments of the invention. The processes described with reference to FIG. 9 may be utilized, for example, in connection with block 840 of FIG. 8. According to one method, template features or samples are identified relative to the fiducial point of the template. The fiducial point, e.g., the R-wave peak, is determined from the rate channel signal of the cardiac beat 905. The cardiac beat is aligned with the template using the fiducial points of the template and the cardiac beat 910. A number of features or samples of the cardiac beat are identified at the locations relative to the fiducial point corresponding to previously determined features of samples of the template 915. The template features or samples and the cardiac beat features or samples may be compared by calculating a feature correlation coefficient (FCC) 920. In one particular embodiment, Equation 1, provided below, is used to compute the FCC between the template features and the beat features.

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [1]$$

where, Xi represents template N features and Yi represents beat N features, and N=8 in this illustrative example. The sign of the numerator term is checked before squaring. If the numerator is negative, the beat is uncorrelated, and the remainder of the computation need not be performed.

If the FCC is greater than a predetermined value, as tested at block 925, for example, about 0.8 to about 0.9, then the cardiac beat is correlated 935 to the template. If the FCC is less than or equal to the predetermined value, then the cardiac beat is uncorrelated 930 to the template. The FCC threshold may be configured to be modified by the physician to tailor the sensitivity and specificity of VT recognition to the needs of a particular patient. Increasing the FCC threshold will require a tighter morphological match and will help discriminate between differing VT morphologies. Lowering the FCC threshold will increase the range of related morphologies that will be associated with and treated with a particular therapy.

Alternatively, a generalized equation may be used for computation of a correlation coefficient in accordance with a correlation waveform analysis (CWA) technique. An equation for calculation of the correlation coefficient (CC) using this technique may be determined according to Equation 2.

$$CC = \frac{N\sum_{i=1}^{N} X_i Y_i - \left(\sum_{i=1}^{N} X_i\right)\left(\sum_{i=1}^{N} Y_i\right)}{\sqrt{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)}} \quad [2]$$

where, Xi represents template N samples and Yi represents signal N samples in this illustrative example.

Figure 10:
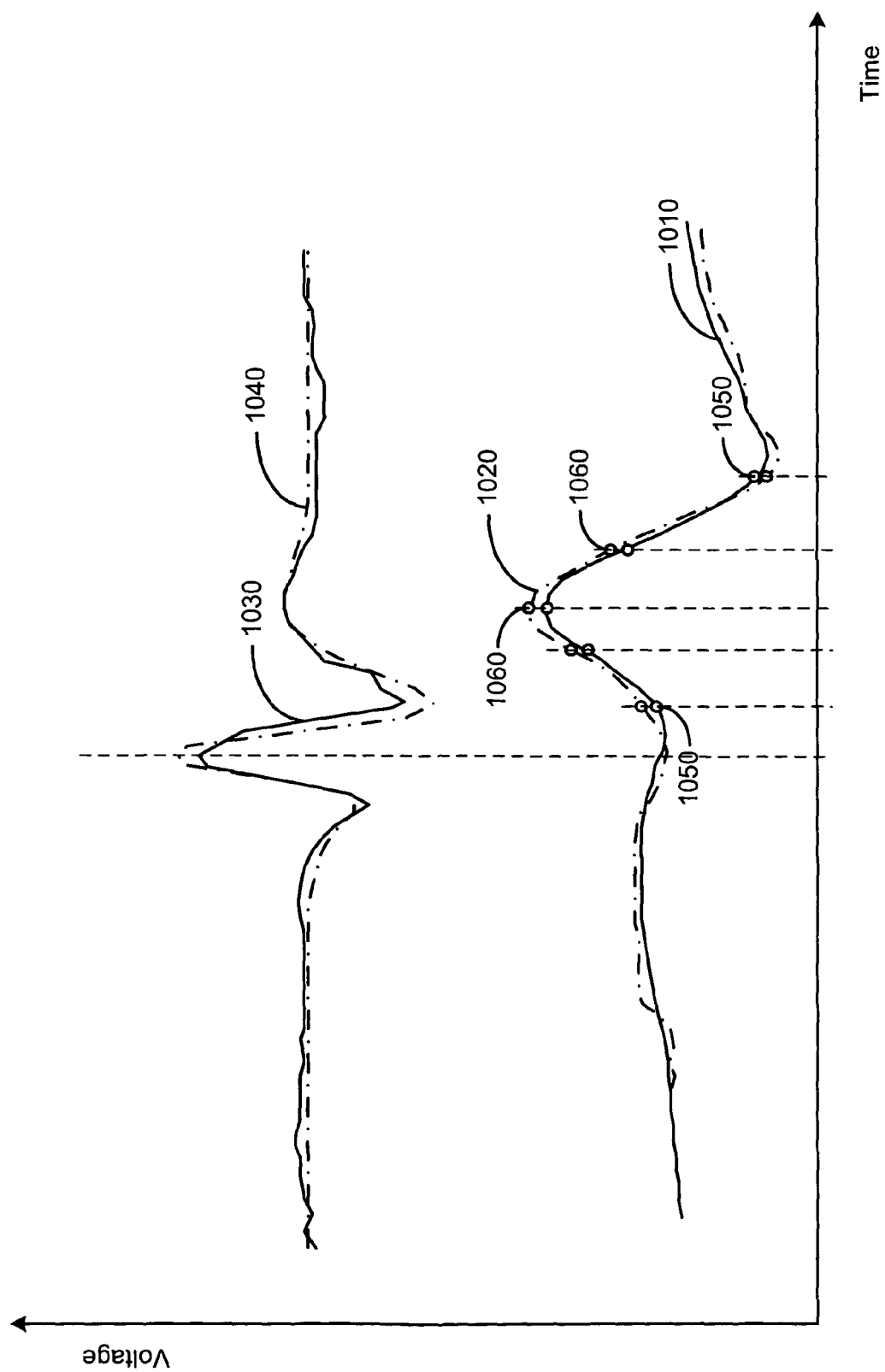
FIG. 10 provides graphs illustrating alignment of rate and shock channel signals of a cardiac beat and an arrhythmia template in accordance with embodiments of the invention.

FIG. 10 provides graphs illustrating rate and shock channel signals corresponding to a VT template and a cardiac beat. To determine correlation between the cardiac beat and the VT template, the shock channel signals of the template 1010 and the cardiac beat 1020 are aligned based on the R-wave peak of the rate channel signals 1030, 1040. Sample points 1050 of the cardiac beat shock channel signal are compared to template sample points 1060. In one implementation, the feature correlation coefficient between the template and the cardiac beat may be calculated as described above using the selected sample points 1050, 1060. If the feature correlation coefficient is greater than a predetermined value, then the cardiac beat is determined to be correlated to the template. If the feature correlation coefficient is less than or equal to the predetermined value, then the cardiac beat is determined to be uncorrelated to the template.

In some situations, modification of one or more arrhythmia discrimination parameters may facilitate classification of types of cardiac rhythms, such as atrial arrhythmia, ventricular arrhythmia, monomorphic VT, and polymorphic VT rhythms. Retrospective analysis of the classification of cardiac rhythms may reveal that some rhythms were misclassified. Misclassification may occur, for example, if an SVT is misclassified as a VT or if a VT is misclassified as an SVT. Misclassification may also occur, for example, if a characterizable arrhythmia is classified as an uncharacterizable arrhythmia or if an uncharacterizable, polymorphic arrhythmia is classified as a characterizable monomorphic arrhythmia.

In some situations, classification may be enhanced by adjusting one or more arrhythmia discrimination parameters. For example, arrhythmia discrimination parameters may involve the number of cardiac beats used to classify the cardiac rhythm, the beat-to-beat stability of the cardiac beats used to classify the rhythm, the rate of the arrhythmia and/or other parameters used in connection with rhythm classification. Rhythm classification may be enhanced by modifying any or all of the arrhythmia discrimination parameters. The rhythm discrimination parameters that improve the identification of various rhythms represent rhythm characteristics that could also be used to further subclassify arrhythmias, and, as a result, fine-tune therapeutic regimens associated with the arrhythmias.

It is believed that the processes described herein may be utilized in connection with many cardiac beat morphology characterization methodologies. Methods and systems for characterizing cardiac beats based on wavelet analysis and feature analysis, aspects of which may be utilized in connection with embodiments of the invention presented herein, are described in U.S. Pat. No. 6,393,316 and U.S. Pat. No. 5,779,645 which are incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating an implantable cardiac system for discriminating between types of arrhythmia affecting one or more heart chambers, the method comprising:

detecting cardiac beats associated with an arrhythmic episode;

comparing a morphology of each cardiac beat to a plurality of representative beat morphologies stored in memory and respectively associated with a plurality of types of monomorphic arrhythmia;

classifying the arrhythmic episode as a particular type of the plurality of types of monomorphic arrhythmia if at least x out of y beat morphologies of the arrhythmic episode are consistent with a representative beat morphology of the particular type of monomorphic arrhythmia based on the comparison, wherein x is a number greater than 1 and y is a number greater than x;

determining that the arrhythmic episode is an unknown type of arrhythmia if the cardiac beats of the arrhythmic episode have been compared to each of the plurality of representative beat morphologies without being matched to any of the plurality of representative beat morphologies based on the comparison;

determining whether or not a representative beat morphology can be acquired for the arrhythmic episode if the arrhythmic episode is the unknown type of arrhythmia;

classifying the arrhythmic episode as a new type of arrhythmia if the arrhythmic episode is determined to be the unknown type of arrhythmia and if the representative beat morphology for the arrhythmic episode can be acquired for the arrhythmic episode; and classifying the arrhythmic episode as an uncharacterizable polymorphic arrhythmia if the arrhythmic episode is determined to be the unknown type of arrhythmia and if the representative beat morphology for the arrhythmic episode cannot be acquired, wherein detecting, comparing, determining, and classifying is performed by the implantable cardiac system.

2. The method of claim 1, wherein comparing the morphology of each cardiac beat to the plurality of representative beat morphologies associated with the plurality of types of arrhythmia comprises comparing the morphology of each cardiac beat to the plurality of representative beat morphologies in an order, the order based on frequency of detection of the arrhythmia types that are respectively associated with the representative beat morphologies.

3. The method of claim 1, further comprising adjusting x as the number of beats of the arrhythmia episode used to classify the arrhythmic episode.

4. The method of claim 1, further comprising selecting between a plurality of therapies for delivery to treat the arrhythmic episode, wherein a first therapy is selected if the arrhythmic episode is classified as one of the plurality of monomorphic arrhythmia types and a different therapy is selected if the arrhythmic episode is classified as polymorphic.

5. The method of claim 1, wherein:

comparing the morphology of each cardiac beat to the plurality of representative beat morphologies comprises comparing the morphology of each cardiac beat to a plurality of representative beat morphology templates; and classifying the arrhythmic episode as the particular type of arrhythmia comprises classifying the arrhythmic episode as the particular type of arrhythmia if the morphologies of the cardiac beats are consistent with a representative beat morphology template associated with the particular type of arrhythmia.

6. The method of claim 1, wherein:

comparing the morphology of each cardiac beat to the plurality of representative beat morphologies comprises calculating a feature correlation coefficient for each cardiac beat; and classifying the arrhythmic episode as a particular type of the plurality of monomorphic arrhythmia types comprises comparing the feature correlation coefficient to a threshold to determine whether each cardiac beat is consistent.

7. The method of claim 6, further comprising modifying the threshold to change sensitivity of arrhythmia recognition.

8. The method of claim 1, wherein x is at least 3.

9. A cardiac arrhythmia classification system, comprising:

a sensor system comprising electrodes for electrically coupling to a heart, the sensor system configured to detect a plurality of cardiac beats associated with an arrhythmic episode of the heart;

memory; and an arrhythmia classification processor coupled to the sensor system, the arrhythmia classification processor configured to compare a morphology of each cardiac beat of the arrhythmic episode to a plurality of representative beat morphologies stored in memory and respectively associated with a plurality of types of arrhythmia and classify the arrhythmic episode as a particular type of arrhythmia if at least x out of y beat morphologies of the arrhythmic episode are consistent with a representative beat morphology of a particular type of arrhythmia based on the comparison, the arrhythmia classification processor further configured to identify the arrhythmic episode as an unknown type of arrhythmia if the cardiac beats of the arrhythmic episode have been compared to each of the plurality of representative beat morphologies without being matched to any of the plurality of the representative beat morphologies based on the comparison and determine whether or not the beat-to-beat morphology of the cardiac beats of the arrhythmic episode are sufficiently consistent to allow a representative beat morphology for the arrhythmic episode to be acquired, the arrhythmia classification processor further configured to classify the arrhythmic episode as a new type of arrhythmia if the arrhythmic episode is identified as the unknown type of arrhythmia and if the representative beat morphology for the arrhythmic episode can be acquired and to classify the arrhythmic episode as an uncharacterizable polymorphic arrhythmia if the arrhythmic episode is the unknown type of arrhythmia and if the representative beat morphology cannot be acquired, wherein the arrhythmia classification system is implantable.

10. The system of claim 9, wherein the arrhythmia classification processor is configured to select between a plurality of therapies for delivery by the cardiac arrhythmia classification system to treat the arrhythmic episode, wherein a first therapy is selected if the arrhythmic episode is classified as one of the plurality of arrhythmia types and a different therapy is selected if the arrhythmic episode is classified as polymorphic.

11. The system of claim 9, wherein the arrhythmia classification processor is configured to compare the morphology of each cardiac beat to the plurality of representative beat morphology templates and classify the arrhythmic episode as the particular type of arrhythmia if the morphologies of the cardiac beats are consistent with a representative beat morphology template associated with the particular type of arrhythmia.

12. The system of claim 9, wherein the arrhythmia classification processor is configured to compare the morphology of each cardiac beat to the plurality of representative beat morphologies in a selected order, the order based on frequency of detection of the arrhythmia types that are respectively associated with the representative beat morphologies.

13. The system of claim 9, wherein the arrhythmia classification processor is configured to compare the morphology of each cardiac beat of the arrhythmic episode to the plurality of representative beat morphologies by calculating a correlation metric for each cardiac beat and classify the arrhythmic episode as a particular type of the plurality of arrhythmia types by comparing the correlation metric to a threshold to determine whether each cardiac beat is consistent.

14. The system of claim 9, wherein x is at least 3.

15. A system for classifying cardiac beats, comprising:
  means for detecting cardiac beats associated with an arrhythmic episode;
  means for comparing a morphology of each cardiac beat to plurality of representative beat morphologies respectively associated with plurality of types of arrhythmia;
  means for classifying the arrhythmic episode as a particular type of the plurality of arrhythmia types if at least x out of y beat morphologies of the arrhythmic episode are consistent with a representative beat morphology of a particular type of arrhythmia based on the comparison, wherein x is a number greater than 1 and y is a number greater than x;
  means for determining that the arrhythmic episode is an unknown type of arrhythmia if the cardiac beats of the arrhythmic episode have been compared to each of the plurality of representative beat morphologies without finding correspondence to any of the plurality of representative beat morphologies; and
  means for classifying the arrhythmic episode as an uncharacterizable polymorphic arrhythmia if the arrhythmic episode is the unknown type of arrhythmia and if the representative beat morphology for the arrhythmic episode cannot be acquired.

16. The system of claim 15, further comprising:
  means for comparing the morphology of each cardiac beat to the plurality of representative beat morphologies by calculating a feature correlation coefficient for each cardiac beat; and
  means for classifying the arrhythmic episode as a particular type of the plurality of arrhythmia types by comparing the feature correlation coefficient to a threshold to determine whether each cardiac beat is consistent.

17. The system of claim 15, wherein x is at least 3.

\* \* \* \* \*